(12) United States Patent
Bakema et al.

(10) Patent No.: US 9,101,274 B2
(45) Date of Patent: Aug. 11, 2015

(54) SENSOR, SENSOR PAD AND SENSOR ARRAY FOR DETECTING INFRASONIC ACOUSTIC SIGNALS

(75) Inventors: Peter Bakema, Grosse Ile, MI (US); Bret Kline, Columbus, OH (US); Alan Langston, Inverness, IL (US); Gary Stephen, Windsor (CA)

(73) Assignee: CVR Global, Inc., Denver, NC (US)

( * ) Notice: Subject to any disclaimer, the term of this patent is extended or adjusted under 35 U.S.C. 154(b) by 94 days.

(21) Appl. No.: 13/167,567

(22) Filed: Jun. 23, 2011
(Under 37 CFR 1.47)

(65) Prior Publication Data

US 2012/0232427 A1 Sep. 13, 2012

Related U.S. Application Data

(60) Provisional application No. 61/358,202, filed on Jun. 24, 2010.

(51) Int. Cl.
| | | |
|---|---|---|
| *A61B 7/00* | (2006.01) | |
| *A61B 7/02* | (2006.01) | |
| *A61B 7/04* | (2006.01) | |
| *B06B 1/06* | (2006.01) | |

(52) U.S. Cl.
CPC ... *A61B 7/04* (2013.01); *A61B 7/00* (2013.01); *A61B 7/003* (2013.01); *A61B 7/02* (2013.01); *B06B 1/06* (2013.01); *A61B 2562/0204* (2013.01)

(58) Field of Classification Search
CPC ..... A61B 7/04; A61B 2562/0204; A61B 7/00

USPC ........................................................ 600/586
See application file for complete search history.

(56) References Cited

U.S. PATENT DOCUMENTS

| | | | |
|---|---|---|---|
| 4,008,711 A | | 2/1977 | Olinger et al. |
| 4,012,604 A | * | 3/1977 | Speidel ..................... 367/180 |
| 4,586,514 A | | 5/1986 | Schlager et al. |
| 4,692,942 A | * | 9/1987 | Morgand ..................... 381/114 |
| 4,770,184 A | | 9/1988 | Greene, Jr. et al. |
| 4,777,961 A | * | 10/1988 | Saltzman ..................... 600/528 |
| 4,928,705 A | | 5/1990 | Sekhar et al. |

(Continued)

FOREIGN PATENT DOCUMENTS

| | | |
|---|---|---|
| CA | 2555838 A1 | 8/2006 |
| EP | 0020110 A1 | 12/1980 |

(Continued)

OTHER PUBLICATIONS

"The History of Blood Pressure Monitoring". www.heathperfect.co.uk/Index/dphistry.htm. Jan. 10, 2006 via www.archive.org.*

(Continued)

*Primary Examiner* — Sean Dougherty
*Assistant Examiner* — Megan Leedy
(74) *Attorney, Agent, or Firm* — Cozen O'Connor

(57) ABSTRACT

A sensor, sensor pad and sensor array for detecting infrasonic signals in a living organism is provided. The sensor, sensor pad and/or array can be utilized for detecting, determining and/or diagnosing level of stenosis, occlusion, or aneurysm in arteries, or other similar diagnosis. The sensor can include unique circuitry in the form of a piezoelectric plate or element sandwiched between two conductive O-rings.

18 Claims, 17 Drawing Sheets

(56) References Cited

U.S. PATENT DOCUMENTS

| | | | |
|---|---|---|---|
| 4,991,581 A | 2/1991 | Andries | |
| 5,010,889 A | 4/1991 | Bredesen et al. | |
| 5,218,969 A | 6/1993 | Bredesen et al. | |
| 5,327,893 A | 7/1994 | Savic | |
| 5,409,010 A | 4/1995 | Beach et al. | |
| 5,511,009 A | 4/1996 | Pastor | |
| 5,515,865 A | 5/1996 | Scanlon | |
| 5,727,561 A | 3/1998 | Owsley | |
| 5,807,268 A | 9/1998 | Reeves et al. | |
| 5,853,005 A | 12/1998 | Scanlon | |
| 5,885,222 A | 3/1999 | Kassal et al. | |
| 5,913,829 A | 6/1999 | Reeves et al. | |
| 6,048,319 A | 4/2000 | Hudgins et al. | |
| 6,053,872 A | 4/2000 | Mohler | |
| 6,149,587 A | 11/2000 | Raines | |
| 6,193,668 B1 | 2/2001 | Chassaing et al. | |
| 6,243,599 B1 | 6/2001 | Van Horn | |
| 6,261,237 B1 | 7/2001 | Swanson et al. | |
| 6,266,071 B1 | 7/2001 | Stam et al. | |
| 6,278,890 B1 | 8/2001 | Chassaing et al. | |
| 6,371,924 B1 | 4/2002 | Stearns | |
| 6,478,744 B2 * | 11/2002 | Mohler | 600/485 |
| 6,478,746 B2 | 11/2002 | Chassaing et al. | |
| 6,520,924 B2 | 2/2003 | Lee | |
| 6,574,494 B2 | 6/2003 | Van Horn | |
| 6,587,564 B1 | 7/2003 | Cusson | |
| 6,607,492 B2 | 8/2003 | Ogura | |
| 6,699,201 B2 | 3/2004 | Stearns | |
| 6,730,030 B2 | 5/2004 | Palti | |
| 6,733,460 B2 | 5/2004 | Ogura | |
| 6,740,043 B2 | 5/2004 | Narimatsu | |
| 6,743,179 B2 | 6/2004 | Narimatsu et al. | |
| 6,748,262 B2 | 6/2004 | Harada et al. | |
| 6,755,792 B2 | 6/2004 | Masuda et al. | |
| 6,758,819 B2 | 7/2004 | Nomura | |
| 6,758,820 B2 | 7/2004 | Narimatsu et al. | |
| 6,780,159 B2 | 8/2004 | Sandler et al. | |
| 6,786,872 B2 | 9/2004 | Narimatsu et al. | |
| 6,793,628 B2 | 9/2004 | Ogura et al. | |
| 6,796,946 B2 | 9/2004 | Ogura et al. | |
| 6,802,814 B2 | 10/2004 | Narimatsu | |
| 6,808,497 B2 | 10/2004 | Ogura et al. | |
| 6,808,627 B2 | 10/2004 | Kawaguchi | |
| 6,814,705 B2 | 11/2004 | Kawaguchi | |
| 6,824,519 B2 | 11/2004 | Narimatsu et al. | |
| 6,827,687 B2 | 12/2004 | Narimatsu et al. | |
| 6,827,688 B2 | 12/2004 | Goto et al. | |
| 6,843,772 B2 | 1/2005 | Nunome et al. | |
| 6,845,263 B2 | 1/2005 | Kawaguchi | |
| 6,869,403 B2 | 3/2005 | Narimatsu et al. | |
| 6,881,190 B2 | 4/2005 | Yamashina et al. | |
| 6,884,221 B2 | 4/2005 | Narimatsu et al. | |
| 6,913,575 B2 | 7/2005 | Nishibayashi et al. | |
| 6,921,368 B2 | 7/2005 | Kawaguchi et al. | |
| 6,923,770 B2 | 8/2005 | Narimatsu | |
| 6,923,771 B2 | 8/2005 | Ogura et al. | |
| 6,939,308 B2 | 9/2005 | Chassaing et al. | |
| 6,955,649 B2 | 10/2005 | Narimatsu | |
| 6,965,355 B1 | 11/2005 | Durham et al. | |
| 6,969,356 B2 | 11/2005 | Nishibayashi | |
| 6,976,966 B2 | 12/2005 | Narimatsu | |
| 7,022,084 B2 | 4/2006 | Ogura | |
| 7,029,442 B2 | 4/2006 | Narimatsu | |
| 7,029,449 B2 | 4/2006 | Ogura | |
| 7,056,291 B2 | 6/2006 | Yokozeki et al. | |
| 7,070,567 B2 | 7/2006 | Mizukoshi et al. | |
| 7,097,621 B2 | 8/2006 | Narimatsu et al. | |
| 7,128,715 B2 | 10/2006 | Narimatsu | |
| 7,131,949 B2 | 11/2006 | Hayano et al. | |
| 7,217,244 B2 | 5/2007 | Suzuki et al. | |
| 7,361,148 B2 | 4/2008 | Narimatsu | |
| 7,621,875 B2 | 11/2009 | Pravica et al. | |
| 8,320,576 B1 * | 11/2012 | Abbruscato | 381/67 |
| 2001/0022757 A1 * | 9/2001 | Skinner et al. | 367/161 |
| 2003/0135084 A1 * | 7/2003 | Young | 600/2 |
| 2003/0208127 A1 * | 11/2003 | Archibald et al. | 600/494 |
| 2004/0171918 A1 | 9/2004 | Suzuki et al. | |
| 2004/0171941 A1 | 9/2004 | Narimatsu et al. | |
| 2004/0171945 A1 | 9/2004 | Narimatsu | |
| 2004/0171947 A1 | 9/2004 | Ogura et al. | |
| 2004/0260193 A1 * | 12/2004 | LaSala | 600/528 |
| 2005/0251047 A1 | 11/2005 | Sleva et al. | |
| 2010/0274099 A1 * | 10/2010 | Telfort et al. | 600/300 |

FOREIGN PATENT DOCUMENTS

| | | |
|---|---|---|
| EP | 0110480 A2 | 6/1984 |
| EP | 1722686 A2 | 11/2006 |
| WO | 8909026 A1 | 10/1989 |
| WO | 2005077004 A2 | 8/2005 |

OTHER PUBLICATIONS

Forsberg, Andrew, et al.; "Immersive Virtual Reality for Visualizing Flow Through an Artery"; Brown University, Providence, Rhode Island; copyright 2000.

Gunawardena, I., et al.; "Why Do Some Patients With >80% Stenosis of the Internal Carotid Artery Not Undergo Surgery? A Retrospective Review"; ANZ. J. Surg. (2001), vol. 71; Jul. 15, 2001; pp. 659-661.

Hill, Stephen L., et al.; "Severe Carotid Arterial Disease: A Diagnostic Enigma"; The American Surgeon; vol. 66, No. 7; Jul. 2000; pp. 656-661.

Abstract of Jadhav, U., et al.; "Non-invasive assessment of arterial stiffness by pulse-wave velocity correlates with endothelial dysfunction"; Indian Heart Journal; vol. 57, No. 3; May-Jun. 2005; pp. 226-232; PubMed PMID: 16196179.

Kisslo, M.D., Joseph A., et al.; "Principles of Doppler Echocardiography and the Doppler Examination #1" teleconference; Duke Center for Echo; publication date unknown; retrieved from http://www.echoincontext.com/basicDoppler.asp on Jul. 12, 2011.

May, Philippe, et al.; "Detection in Hemodynamic Turbulence in Experimental Stenosis: An in vivo Study in the Rat Carotid Artery"; J. Vasc. Res., 2002, vol. 39; pp. 21-29.

Pravica, D., et al.; "Current Market Research for Pravica and Day"; Research notes discussing background, market information, current diagnostic technology and competitors in the market and potential licensees, containing article titled "Computer Recognizes Abnormal Heart Sounds in Children," by DeGroff, Curt G., M.D., et al.; published Jun. 5, 2001 by American Heart Asociation.

DeGroff, Curt G., M.D., et al.; "Computer Recognizes Abnormal Heart Sounds in Children"; American Heart Association; Jun. 5, 2001; retrieved from Science Daily on Jul. 11, 2011; http://www.sciencedaily.com/releases/2001/06/010605075834.htm.

Kuriyama, K., et al.; "Omron Healthcare Launches Non-Invasive Vascular Diagnostic System for Cardiovascular Disease Management"; published Mar. 28, 2006; retrieved Jul. 11, 2011 from http://www.pcronline.com/News/Press-releases/OMRON-HEALTHCARE-Launches-Non-Invasive-Vascular-Diagnostic-System-For-Cardiovascular-Disease-Management.

International Search Report for PCT/US2011/003873 mailed Dec. 11, 2006.

International Preliminary Report on Patentability for PCT/US2011/003873 mailed Feb. 6, 2007.

Written Opinion of International Searching Authority for PCT/US2011/003873 mailed Dec. 11, 2006.

International Search Report for PCT/US2011/041678 mailed Nov. 28, 2011.

Written Opinion of International Searching Authority for PCT/US2011/041678 mailed Nov. 28, 2011.

* cited by examiner

SENSOR, SENSOR PAD AND SENSOR ARRAY FOR DETECTING INFRASONIC ACOUSTIC SIGNALS

CROSS-REFERENCE TO RELATED APPLICATIONS

The present Application claims the benefit of U.S. Provisional Application No. 61/358,202 filed Jun. 24, 2010, the relevant contents of which are incorporated herein by reference.

FEDERALLY SPONSORED RESEARCH OR DEVELOPMENT

N/A

FIELD OF THE INVENTION

The present invention generally relates to an infrasonic sensor, sensor pad and sensor array for holding a plurality of sensors in a set configuration. The sensor, pad and/or array can be utilized, for example, for non-invasive sensing and recording of blood flow and other related signals at very low hertz levels. The sensed information can be used to detect the level of stenosis, occlusion or aneurysm, if any, of arteries and other related diagnosis of a living organism.

BACKGROUND OF THE INVENTION

Infrasonic acoustic signals generated by a living organism can be useful in the detection and diagnosis of certain conditions or ailments of the organism. In particular, blood flow in the organism cause infrasonic acoustic signals (e.g., via vibration of the arterial or venal walls) that indicate possible extent of stenosis, occlusion or aneurysm in the organisms' arteries and/or veins.

U.S. Pat. No. 7,621,875 describes one process for detecting arterial disease using sensed infrasonic acoustic signals. As described therein, sensed infrasonic signals are analyzed by a computer or other similar device to generate a complex frequency grid of frequencies and associated lifetimes. A predictive model of complex frequencies associated with peak-perturbation acoustic signals attributed to boundary perturbations in vivo that occur with early stage arterial disease is provided. A predictive model of complex frequencies associated with line-perturbation acoustic signals attributed to boundary perturbations in vivo that occur with later stage arterial disease is also provided. It is then determined whether peak and/or line-perturbation acoustic signals of the predictive models are present to detect whether the subject has arterial disease.

U.S. Pat. No. 5,853,005 discloses known transducers and acoustic pads for sensing acoustic signals in an organism. The devices shown in U.S. Pat. No. 5,853,005 are difficult to utilize, and can generate signal noise and/or spikes which can be disruptive in proper analysis.

Quickly and easily setting up equipment to sense any acoustic signals at the proper locations on a subject can be of vital importance in an emergency. Even in non-emergency situations, ease of use is important in that it enables a medical technician (or possibly a patient) to administer the procedure and utilize the equipment without a doctor having to be present.

The present invention provides an improved sensor, sensor pad and sensor array for sensing infrasonic acoustic signals.

SUMMARY OF THE INVENTION

The present system includes a sensor, a sensor pad and a sensor array (holding a plurality of sensors) for the passive detection of infrasonic signals generated by a living organism. In one embodiment, these components are combined with a touch panel PC (i.e., a main computing unit) with applications that interpret a sound signature from the sensor array, and analyze the sound features and spectrum to determine or define the severity of stenosis, or narrowing within an artery, occlusion, 100 percent closure, or aneurysm. In one embodiment, the sensor array is designed to detect occlusion in the carotid arteries.

The sensor array is a highly sensitive acoustic capturing device, capable of receiving sound waves internal to the body that passively flow at a frequency range of <1-20 hz. The sensor array is adjustably configured to account for the anatomical differences between individuals, to filter external noise and amplify the sound signature emitting passively from the human body. In accordance with one embodiment, the sensor array in collaboration with the software or application running on the PC or main computing unit, takes three readings simultaneously from the right and left carotid arteries in the neck and from the heart just below the sternum, calibrates the sound signature, filters and then digitizes data for analysis. A shielded cable transmits the signals to the main computing unit. The sensor array is adjustably designed to fit any adult person and be held by the patient for the test. There is no effect upon blood circulation while the test is being conducted. Most significantly, the system is designed to be a passive test that is non-emitting, non-invasive, and is configured so that anyone can conduct the test without requiring certification.

Utilizing certain algorithms, such as those disclosed in U.S. Pat. No. 7,621,875 or other similar algorithms, the present components can be utilized in a system to identify the systolic event, calibrate the signal, analyze the signal utilizing low frequency (Spectral) methods and assess the range of stenosis, occlusion or aneurysm within each carotid artery. The system first goes through a series of calibration steps, in concert with the sensor array, ensuring correct receipt of the signals, correlating the signals from the two carotid arteries and the heart, and identifying the systolic time, the period of most rapid fluid flow. Once the signal is recorded, the system prepares the data for processing the digital signal to conduct a spectral analysis. Using the signal features, a statistical analysis is performed against multiple parameters to render a classification of degree of stenosis, occlusion or aneurysm within each carotid artery. The output renders a report indicating a range of blockage against the defined Nascet categories with a representation of the systolic events.

In accordance with one embodiment, the sensor array includes three sensors, two of which are positioned proximate the carotid arteries and one below the sternum. The array includes a structure having three branches for holding the sensors. The upper two branches or arms are flexibly connected to the third branch or base to allow for adjusting the sensors to properly position each sensor on the carotid arteries of bodies of different sizes. In this regard, the upper two branches are biased inward and can be bent/flexed outward to the proper position. To accommodate bodies of differing heights, additional modifications can be made to allow for the adjustment of the lower sensor with respect to the upper sensors (e.g., providing a telescoping or otherwise extendable portion or arrangement in the lower branch and/or the upper two branches).

The sensors in the array are designed to be readily replaceable. Each sensor includes a disk shaped circuit between two conductive O-rings. Each sensor also includes a bag-type gel pack or pad, or a solid gel pack or pad. The pad is used for contact with the body. The pads are meant to be disposable after each use, and the sensors require replacement after about 50-100 uses.

In accordance with an embodiment of the invention a sensor pad for transmitting infrasonic acoustic signals to a sensor is provided. The sensor pad comprises a bottom wall having a flat circular surface for contact with a piezoelectric element. The pad also includes a contacting portion connected to the bottom wall. The contacting portion has a circumferential side wall extending upward from the bottom wall to a forward facing contacting surface. Additionally, the contacting portion includes a first outwardly concave region forming an indentation or dimple in the contacting portion. The outwardly concave region can be on the forward facing contacting surface of the contacting portion. In this configuration a rim forms around the concave portion and is typically the first part of the pad that comes into contact with a body during use.

The pad is formed from a soft material having a low durometer value. The pad is configured to allow material in the pad to flow into the first outwardly concave region upon contact with a surface, such as a body. By allowing the material to flow in this region, pressure from the initial contact does not cause material to press against the bottom wall connected to the sensor.

In one embodiment the pad is formed as a liquid filled bag. The pad comprises a first sheet forming the bottom wall and a second sheet connected to the first sheet forming an outer wall of the contacting portion. The liquid is positioned in the interior of the bag formed by the two sheets. The sheets can be vinyl films or other similar materials, and the liquid interior can be a liquid silicon.

The sensor pad can also comprise a lip portion circumferentially around the bottom wall extending radially outward past the side wall of the contacting portion. The sensor pad can be formed with only one outwardly concave region or it can include a second or third outwardly concave region in the contacting portion. In fact, it can have a plurality of concave portions in the contacting portion. Moreover, such regions can be formed in the contacting surface and/or in the side wall of the pad.

In a separate embodiment, the pad is completely formed from a partially solidified gel, such as a silicon gel. The bottom wall or surface of the pad is preferably tacky, enabling it to stick to a sensor element.

In accordance with yet another embodiment, a disposable sensor pad for transmitting acoustic signals from a body to a sensor is provided. The pad comprises a circular disk of a low durometer value material having an upper contacting portion for contacting a body. The upper contacting portion includes a circumferential side wall and a circular upper surface. The upper contacting portion also includes an indentation devoid of material. The pad further includes a bottom portion having a flat circular surface connected to the upper contacting portion for contacting a sensor element. The indentation can be a first outwardly concave region in the forward facing surface of the contacting portion.

The circular disk can be formed from two sheets of vinyl film filled with a silicon liquid. Alternatively, the circular disk can be formed from a partially solidified silicon gel. A lip can extend circumferentially around the disk radially outward from the side wall of the contacting portion.

In accordance with another embodiment of the invention, a sensor pod for sensing acoustic signals is provided. The sensor pod comprises a housing having an interior chamber and a circular opening. A piezoelectric element in the form of a circular disk having a first side and an opposing second side is contained in the interior chamber of the housing and is aligned with the circular opening. The piezoelectric element comprises a metal plate with a ceramic material contacting a side of the plate.

A first O-ring is positioned on and in contact with the first side of the piezoelectric element and, a second O-ring is positioned on and in contact with the second side of the piezoelectric element, maintaining the piezoelectric element between the O-rings. One or both of the O-rings can be electrically conductive and comprise an electrically conductive material. One example of an electrically conductive material is a metalized rubber. A first conductive contact element can be embedded or otherwise connected to the housing, and be electronically coupled to the first O-ring for transmitting signals generated by the piezoelectric element. A second contact element can be utilized for the second O-ring.

The housing can comprise a first upper housing portion connected to a second lower housing portion. Each portion can also be formed from one or more components. Preferably, the housing portions have a circular top view configuration centered about the circular opening.

The sensor pod can further comprise an acoustic coupling pad having a flat surface contacting the first side of the piezoelectric element and a body contacting portion extending through the circular opening in the housing. Pads as described herein are preferred, however, other types of acoustic pads (such as a simple cylindrical disk of appropriate material lacking some of the structural features described above) may work with the sensor pod.

An amplifier circuit electrically coupled to the piezoelectric element can be contained in the interior chamber of the housing. The amplifier circuit can be, for example, on a board. Other similar circuitry could also be similarly positioned in the chamber.

The housing further comprises a swivel connector extending from a bottom portion of the housing. The swivel connector enables the pod to be connected to a support structure, such as the arrays disclosed herein, and enables the pod to pivot about the connection. Other types of connections can also be implemented with the pod.

In accordance with another embodiment of the invention, a sensor pod for sensing infrasonic acoustic signals in a living organism is provided. The sensor pod comprises a sensor housing having an internal chamber and an opening. A piezoelectric element is mounted in the internal chamber. The piezoelectric element comprises a metal plate having a first side and an opposing second side. The first side of the plate has a piezo-type material coating at least a portion of the first side. The piezoelectric element is positioned to span across the opening, essentially dividing the internal chamber into an outer chamber portion configured to receive an acoustic coupling pad and an inner chamber portion. An amplifier circuit is mounted in the inner chamber portion of the housing and electrically coupled to the piezoelectric element. The housing comprises a metal surface around the inner chamber portion such that the metal surface of the housing and the metal plate of the piezoelectric element form a faraday cage around the amplifier circuit.

The housing can comprise a first housing portion and a second housing portion connected to the first housing portion. In this configuration, the inner chamber portion is preferably formed in the second housing potion. Other aspects of the other embodiments described can also be utilized in this embodiment.

The sensor pod can further comprise a low durometer value pad having a bottom wall positioned against the first side of the piezoelectric element and a contacting portion connected to the bottom wall which extends outward through the opening in the housing. The contacting portion of the pad includes an outwardly concave region.

In accordance with yet another embodiment of the invention, a sensor array for positioning a plurality of acoustic sensors on a living organism is provided. The sensor array comprises a sensor support structure having a base portion which includes a first connection element for connecting a first sensor to the base portion. A first arm extends from the base portion and includes a second connection element for connecting a second sensor to the first arm. A second arm also extends from the base portion and includes a third connection element for connecting a third sensor to the second arm. The sensor pods described herein can be used as the sensors to be connected to the array.

The support structure is configured to position the first, second and third sensors at appropriate locations on the living organism. To facilitate proper positioning, the first arm and the second arm flexibly connected to the base portion. Additionally, the first arm and second arm can be adjustable to enable movement between the sensors. In this regard, one or both arms can be extendable, such as by a telescoping feature. Similarly, the base portion can be configured to include a tongue portion (which holds the sensor) which can be extendable.

The sensor array can further comprise a handle formed in the support structure to enable a user to grasp the sensor array and hold it in a proper location. In one embodiment, the base portion can also be used as a handle.

The first, second and third connection elements can be configured to mate with a swivel ball connector on a sensor pod housing. Other connection means could be also used.

The support structure is configured to enable a cable or other electrical connection to transmit signals generated by the sensors to a computing device for analysis and/or display. In this regard, the base portion can be hollow or otherwise include a path for placement of a cable or other conductive element for transmitting signals generated by a sensor connected to the first connecting element to a computing device. Similarly, the first and second arms can be hollow or otherwise include a path for placement of a cable or other conductive element for transmitting signals generated by a sensor connected to the second connecting element to the computing device.

The sensor array can be formed from a hard plastic. Other suitable materials can also be used.

In other embodiments, the array can include more or fewer connections for sensors. Similarly, the array can include more or less arms depending on the number of sensors needed. The arms can be positioned in configurations to employ the sensors in the needed positions. Moreover, each arm can include more than one sensor, if needed. The sensors can be mounted to be slidably and/or rotatably attached to the arm.

In accordance with another aspect of the invention, an assembly for converting acoustic signals into electrical signals is provided. The assembly comprises a thin disk-shaped piezoelectric element. The element includes a circular metal sheet having a first side and an opposing second side, and a first radius. The metal sheet can be a stainless steel or other similar or suitable materials. A piezo-type material is connected to or coated on the first side. The assembly further includes a first conductive O-ring abutting the piezo-type material on the first side of the metal sheet, and a second conductive O-ring abutting the second side of the metal sheet. The first and second O-rings can be formed from a metalized rubber.

The piezo-type material can be a ceramic material. The ceramic material can be configured in circular pattern located in the center of the first side of the metal sheet. Additionally, the ceramic material can be configured to define a plurality of distinct (i.e., discrete, or non-touching) sections devoid of material. The ceramic material can be configured in at least two sections, or can have three, four or twelve sections. Other configurations having different numbers of sections can be used. Preferably the number is chosen to maintain balance in the piezoelectric element. The centrally located ceramic material includes two or more segments that extend radially outward to contact the first O-ring. The segments can be used to define the sections devoid of material. The segments can extend from the centrally located ceramic material to an outer ring of ceramic material proximate an outer edge of the disk.

The assembly can be electronically coupled to an amplifier circuit through the first and second O-rings. In one embodiment, the first O-ring acts as an electrically positive lead for the assembly and the second O-ring acts as a negative or ground lead for the assembly.

Further aspects of the invention are disclosed in the description of the invention including the Figures.

BRIEF DESCRIPTION OF THE FIGURES

To understand the present invention, it will now be described by way of example, with reference to the accompanying Figures and attachments in which.

DETAILED DESCRIPTION OF THE INVENTION

While this invention is susceptible of embodiments in many different forms, there is shown in the Figures and will herein be described in detail preferred embodiments of the invention with the understanding that the present disclosure is to be considered as an exemplification of the principles of the invention and is not intended to limit the broad aspect of the invention to the embodiments illustrated.

The present invention provides a sensor—in the form of a sensor pod—for detecting infrasonic acoustic signals created or generated by a living organism, such as signals caused by blood flow through one or more veins or arteries. The invention also includes improved gel packs or pads utilized with the sensor. The pads act as an acoustic coupling mechanism between the sensor and the living organism. The pads are made from materials designed to match a body's impedance to allow acoustic signals to pass efficiently to the sensor. Additionally, the invention includes a sensor array containing one or more sensors. The array is utilized to allow someone (and in some cases the patient) to easily and quickly place and hold the sensors in appropriate locations on the living organism to detect signals generated by the organism. The array is preferably designed to be adjustable to fit living organisms of varying sizes.

The sensors, pads and arrays of the present invention are useful in detecting signals in the living organism that can be analyzed to determine various medical conditions. As noted above, U.S. Pat. No. 7,621,875 discloses one use for detecting and diagnosing possible stenosis, occlusion, aneurysm or other shape of wall irregularity in certain arteries.

Figure 1:
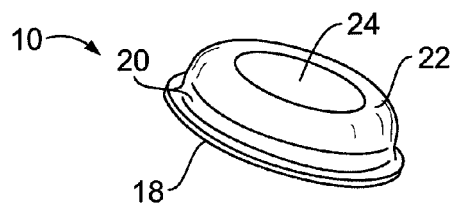
FIG. 1 is top perspective view of a sensor pad in accordance with the present invention.

FIG. 1 shows a sensor pad 10 having a generally circular shape in accordance with the present invention. The sensor pad 10 is design to contact a body of a living organism at a desired location and transmit acoustic signals from the body to a piezoelectric plate of a sensor (discussed in more detail below). The pad 10 is designed to match the impedance of the body to enable efficient transfer of signals (while it is contemplated that the disclosed sensors, pads and arrays could be used—either separately or in combination—with many types of living organisms, and possibly inanimate objects, the use of these components will be predominately described with respect to detection of signals generated by a human body). Such impedance matching reduces reflection of any sound waves and facilitates maximum signal transfer to the sensor.

Figure 2:
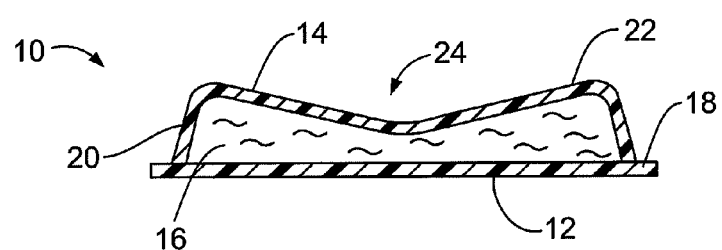
FIG. 2 is a cross-sectional view of a first embodiment of the sensor pad of FIG. 1.

Referring also to the cross-section of FIG. 2, one embodiment of the sensor pad 10 is in the form of a flexible, soft bag filled with a gel or liquid. The bag is formed from a first, circular flat sheet or layer 12 of vinyl forming a bottom wall, and a second, outer sheet or layer 14 of vinyl forming a body contacting portion. A silicon based fluid or gel 16 is contained between the two layers 12, 14. The pad 10 includes a lip 18 which is formed from a portion of the first, flat layer 12 extending radially outward from a location where the outer layer 14 contacts the flat layer 12. The lip 18 extends circumferentially around the pad 10.

The outer layer 14 includes a side wall 20 that extends upward from the flat layer 14 to a rim 22 (directional terms, such as "upward" are used herein to help describe features of the components as shown in the drawings and are not meant to limit the invention—many of the components will be used in multiple orientations). The top portion of the outer layer 14 includes an outwardly concave indentation or dimple 24.

Figure 21:
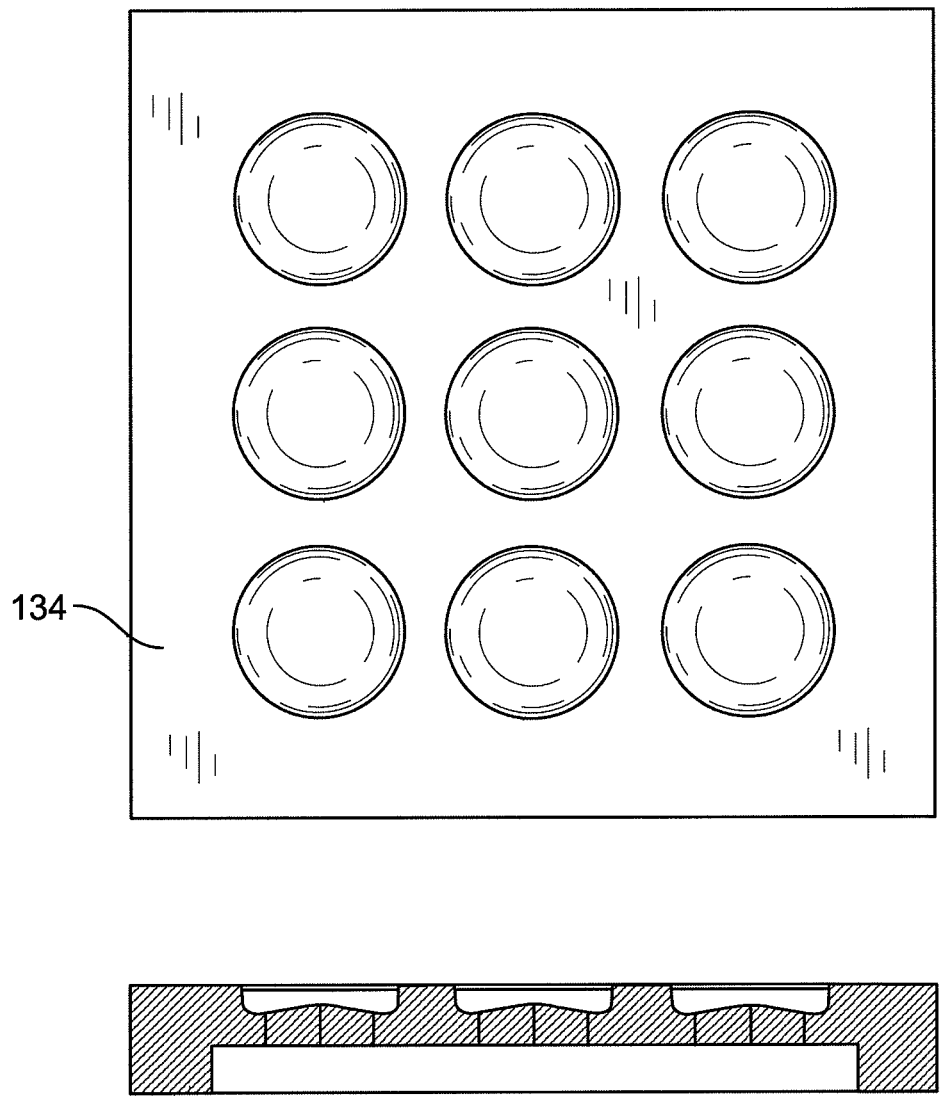
FIG. 21 is a top plan view and a cross-sectional view of a mold for forming sensor pads in accordance with an embodiment of the invention.

The outer sheet 14 initially starts as a flat sheet of material that is vacuum formed into a mold 134 having the desired outer shape of the pad 10 (see FIG. 21 for a top plan view and a cross-sectional view of a plurality of molds 134 for forming the pad 10). The silicon gel or liquid 16 is then added, and the flat layer 12 is positioned over the outer layer 14 and gel/liquid 16. The flat layer 12 is then vacuum sealed to the outer layer 14. This process causes the outer layer 14 to slightly melt into the flat layer 14 where they contact each other.

In use, the flat layer 12 of the pad 10 is positioned against the outer surface of the piezoelectric plate or element of the sensor (again, discussed in more detail below). Portions of the outer layer 14 are used to contact the body to sense acoustic signals.

Figure 4:
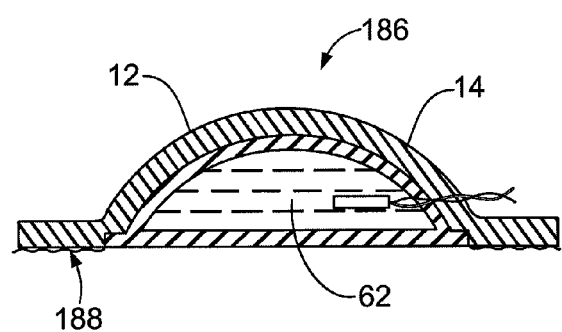
FIG. 4 is a cross-sectional view of a prior art sensor pad.

A prior, bag-type sensor pad (FIG. 30 from U.S. Pat. No. 5,853,005) is shown in cross-section in FIG. 4. The reference numbers provided in FIG. 4 were the ones designated in U.S. Pat. No. 5,853,005 and are not related to the reference numbers used to describe the present inventions. As shown, the prior pad (designated as 186) includes a domed, outwardly convex outer surface—which is used to contact a portion of the body. Upon such contact, when the outer surface of this prior pad meets resistance from the body the domed shape compresses, forcing fluid or gel in the bag back into the flat base surface on the bottom of the pad. This, in turn, causes the flat surface to distort (i.e., bend outward) and press into the sensor. The distortion of the flat surface results in an undesired acoustic spike or noise by the sensor.

In contrast to the prior art pads, the present pad 10 includes the concave indentation or dimple 24. Upon contact with a body, gel or liquid is dispersed evenly into the dimple region allowing the flat layer 12 to remain flat and not distort under typical use.

While a centrally located indentation or dimple 24 is shown in the Figures, the pad 10 could have alternative configurations that create the same benefits. For example, the pad 10 could include additional dimples, or could have a plurality of smaller dimples rather than the large central dimple. Additionally, the dimples or indentations could be formed in different locations, such as in the side wall 20 of the outer layer 14.

Figure 3:
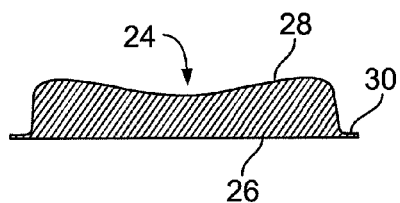
FIG. 3 is a cross-sectional view of a second embodiment of the sensor pad of FIG. 1.

A second embodiment of the pad 10 is shown in cross-section in FIG. 3. This pad includes a flat, bottom surface 26, and an upper contacting surface 28. A rim 30 can extend around the outer contacting surface proximate the flat, bottom surface 26.

The second pad embodiment has generally the same (or substantially similar) outer shape as the fluid filled, bag-type sensor pad shown in FIG. 2. However, in this embodiment, the pad 10 is completely formed from a partially solidified gel or liquid, such as silicon. Accordingly, the sensor pad 10 of FIG. 3 is of one-piece construction. Notwithstanding this, the pad operates in a similar manner as the bag-type embodiment. That is, material in the pad moves or fills in the indentation or dimple region upon contact with a body rather than distorting the bottom flat surface (i.e., the sensor contacting surface).

Preferably, the sensor pad 10 has a "tacky" bottom surface, allowing it to stick to the piezoelectric element of the sensor in use. Because the tacky surface allows the pad to stick to the sensor, it may not be necessary to provide the lip 30 in this embodiment.

The pad of FIG. 3 can be formed from a single partially solidified material. Alternatively, it may be possible to use more than one partially solidified material to form the pad. The materials could be combined or formed in layers or other similar arrangements.

In both embodiments, the pads are designed to be very soft, having a low durometer value (e.g., in the range of 1-2 durometers). While soft silicon and vinyl materials are suitable for forming the pads (as discussed above), other similar—low durometer—materials may also be used.

Figure 5:
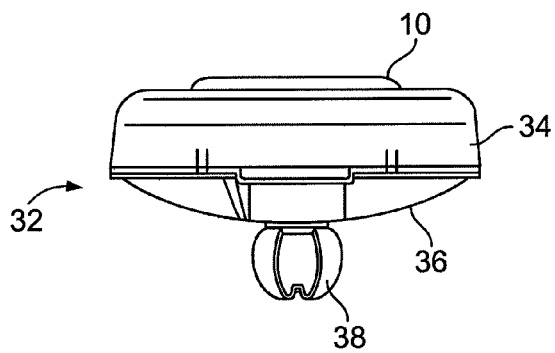
FIG. 5 is a side view of a sensor or sensor pod in accordance with the present invention.
Figure 6:
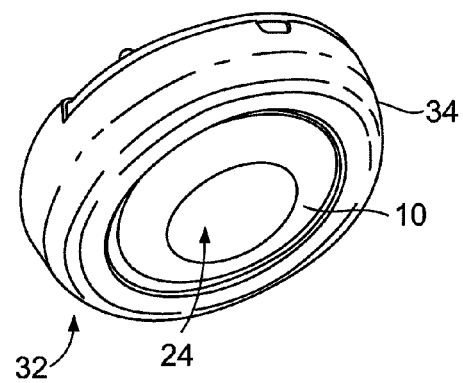
FIG. 6 is a perspective view of the contacting portion of the sensor pod of FIG. 5.

The sensor pads 10 are preferably used as part of a sensor or sensor pod 32 shown in FIGS. 5-8. As illustrated in FIG. 5, the sensor pod 32 includes a housing having a first upper housing portion 34 and a second lower housing portion 36 connected to the first housing portion 34 (again, terms such as "upper" and "lower" are used with reference to certain Figures and are not meant to limit the sensor pod to any particular orientations). The housing portions 34, 36 can be of single piece construction or can include multiple components or pieces.

A swivel connector 38 is connected to or integrally formed as part of the second housing portion 34. The swivel connector 38 is used to connect the sensor pod 32 to a sensor array and allows the sensor pod to pivot to an appropriate position in use. The housing portions 34, 36 can be formed from an injection molded plastic.

Figure 7:
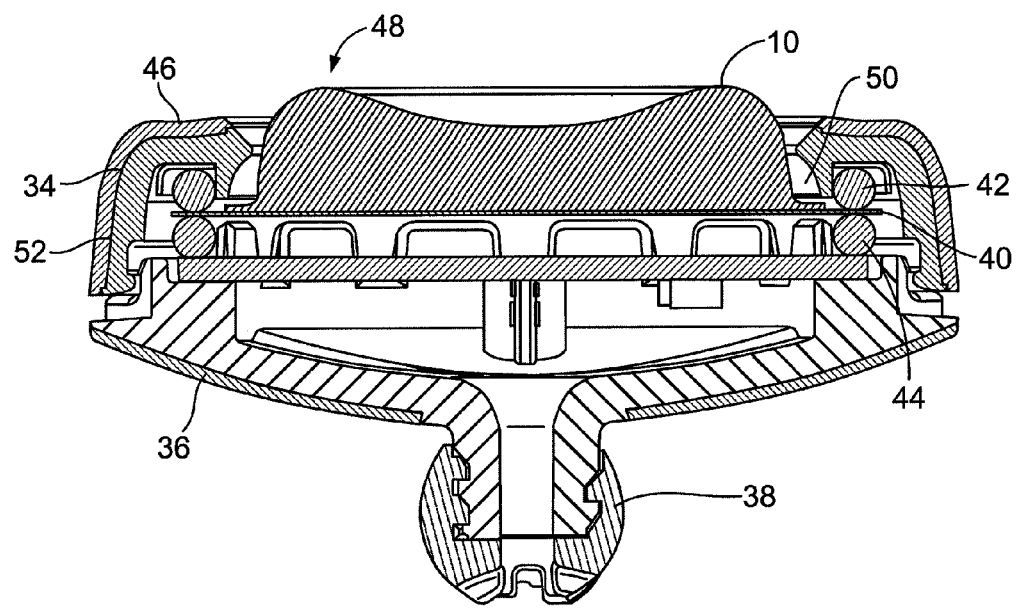
FIG. 7 is a cross-sectional view of the sensor pod of FIG. 5.
Figure 8:
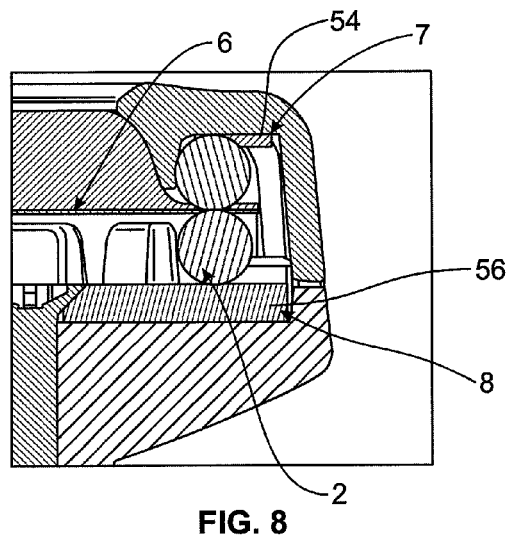
FIG. 8 is an enlarged portion of the cross-sectional view of FIG. 7.

Referring also to FIGS. 7 and 8, the flat surface of the sensor pad 10 is placed in contact with a piezoelectric element 40. The contacting surface or portion of the sensor pad 10 extends above or outward from the first housing portion 34, and can be placed in contact with a body. The pad 10 acts as an acoustic coupling mechanism and relays acoustic signals sensed in the body to the piezoelectric element 40.

The piezoelectric element 40 is in the form of a circular metal plate having a ceramic coating on a first or upper side of the plate, however other piezo-type materials can be utilized. The piezoelectric element 40 is supported between a first or upper O-ring 42 and a second or lower O-ring 44. The O-rings 42, 44 are formed from a metalized rubber and are used to conduct electrical signals generated by the piezoelectric element 40 in response to infrasonic acoustic signals from the body. The O-rings 42, 44 replace direct contact wires that were typically soldered to portions of the plate.

The arrangement of the O-rings 42, 44 about the piezoelectric element 40 allows the piezoelectric element 40 to more freely vibrate and bend in response to sensed acoustic signals than it would have if direct contact wires were utilized. In this regard, the O-rings 42, 44 do not rigidly hold the piezoelectric element 40. The first O-ring is designed to abut or contact only the piezo-electric material on the first side of the metal plate. Accordingly, the radius of the O-ring should be chosen to with the radius and pattern of the coating material in mind. Additional aspects of the piezoelectric element 40 and O-rings 42, 44 are discussed in more detail below with respect to FIGS. 12-17.

The first housing portion 34 presents a circular face 46 with a central opening 48. As mentioned, an upper contacting portion of the pad 10 extends outward from the sensor pod 32 through the central opening 48 in the first housing portion 34. The first housing portion 34 further includes an inwardly directed, circumferential segment 50 extending from the face 46 toward the piezoelectric element 40. The inwardly directed segment 50 can be sized to extend over the lip 18 of the pad 10 to secure the pad 10 to the sensor pod 32. Again, if the pad 10 has a tacky bottom wall it may not be necessary to include the lip 18 in order to maintain the pad 10 in position on the sensor pod 32.

The first housing portion 34 also includes a circumferential outer side wall 52 which can be clipped, screwed or otherwise attached to the second housing portion 36. The combined housing portions 34, 36 form a chamber for holding the piezoelectric element 40 and pad 10. The chamber also contains an amplifier board having an amplifier circuit for amplifying the signals generated by the piezoelectric element 40 and transmitting them to a computer (or other similar device) for analysis and/or display. In order to shield the amplifier board from noise and other stray signals, the housing portions 34, 36 are provided with a metal surface which, when combined with the metal plate of the piezoelectric element 40, form a Faraday cage around the amplifier board and any other circuitry positioned in the chamber.

Referring to FIG. 8, the first housing portion 34 includes a first conductive contact element 54 which is positioned to be in contact with the first O-ring 42. The second housing portion 44 similarly includes a second conductive contact element 56 in contact with the second O-ring 44. The conductive elements 54, 56 relay the signals to the amplifier board which in turn passes the amplified signal—preferably via shielded cable—to the computer. The first and second conductive contact elements 54, 56 can be in the form of metal rings secured in appropriate positions in the respective housing portions. One or both of the conductive contact elements can be spring loaded to maintain proper contact with the corresponding O-ring.

Figure 9:
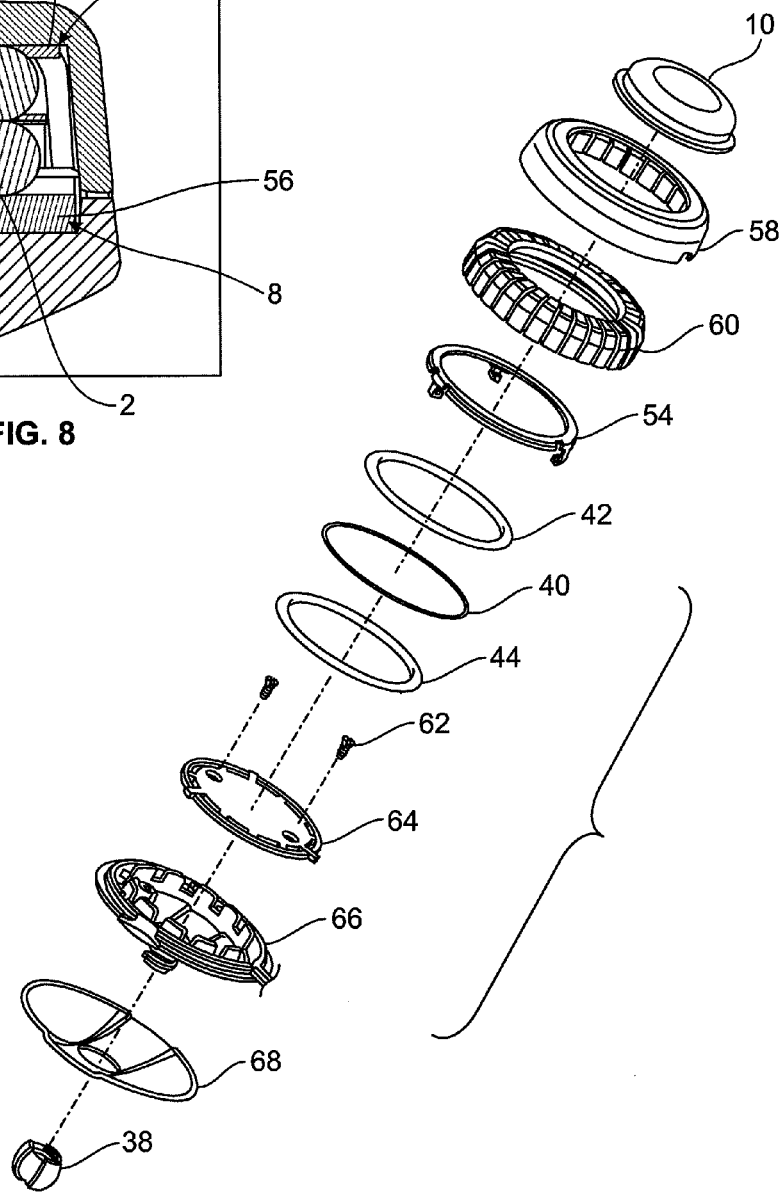
FIG. 9 is an exploded view of an embodiment of a sensor or sensor pod in accordance with the present invention.

FIG. 9 discloses an exploded view of one embodiment of the sensor pod 32. Starting at the top, the sensor pod 32 of FIGS. 5 and 6 includes a pad 10 followed by an outer portion 58 of the upper housing portion 34 and an inner portion 60 of the upper housing portion 34. Below the inner portion 60 is the first conductive contact element 54, followed by the upper O-ring 42, the piezoelectric element 40 and the lower O-ring 44. Two screws 62 are aligned with holes in a PCB assembly 64 positioned below the lower O-ring 44. An inner portion 66 of the lower housing portion 36 and an outer portion 68 of the lower housing portion 36 follow, with the swivel ball or connector 38 at the lowest point.

Figure 10:
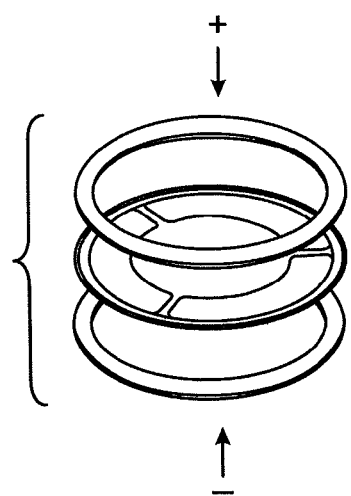
FIG. 10 is an exploded perspective view of an O-ring—piezoelectric element assembly.
Figure 11:
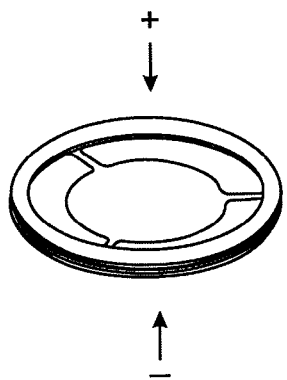
FIG. 11 is a perspective view of the O-rings and piezoelectric element of FIG. 10 assembled.
Figure 12:
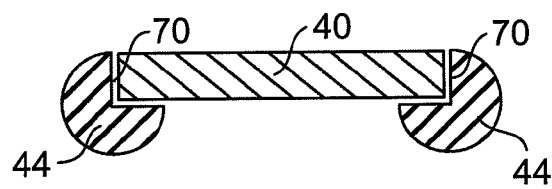
FIG. 12 is a cross-sectional view of a modified O-ring with a piezoelectric element in accordance with a further embodiment of the present invention.

FIG. 10 discloses an exploded view of one embodiment of the O-rings 42, 44 and piezoelectric element 40, and FIG. 11 shows these components in an assembled state. The O-rings and piezoelectric element form an assembly that freely holds the piezoelectric element for optimal transmission of the sensed acoustic signals (this assembly formation—using O-rings—can also be utilized with other piezo-type devices and is not necessarily limited to the sensors and uses described with respect to the preferred embodiments herein).

In this assembly, the upper O-ring 42 is the positive conductive element and the lower O-ring 44 is the negative or ground conductive element.

In accordance with a further embodiment of the invention, one or both of the O-rings can be modified to include structure to more effectively maintain the piezoelectric element 40. As shown in cross-section in FIG. 12, the second O-ring 44 is provided with a circumferential channel or groove 70. The radius of the O-ring is set so that the edges of the piezoelectric element 40 sit in the channel 70.

Another key to optimal transmission of the sensed acoustic signals is for the O-ring—piezoelectric element assembly to be balanced. When wires are soldered to the piezoelectric element (in instances where O-rings are not used), the element is not necessarily balanced which can impair the acoustic signal.

Balancing of the piezoelectric element 40 is further enhanced by the pattern of the ceramic or other piezo-type material used. As shown in FIGS. 13-17 piezoelectric element 40 is provided with a centrally located region of ceramic coating 72 surrounded by two or more distinct (i.e. separate) sections 74 devoid of the ceramic material. Each section is defined by a spoke or segment 76 of material on either side extending radially from the centrally located region to a rim or edge of the metal plate of the piezoelectric element 40.

Figure 13:
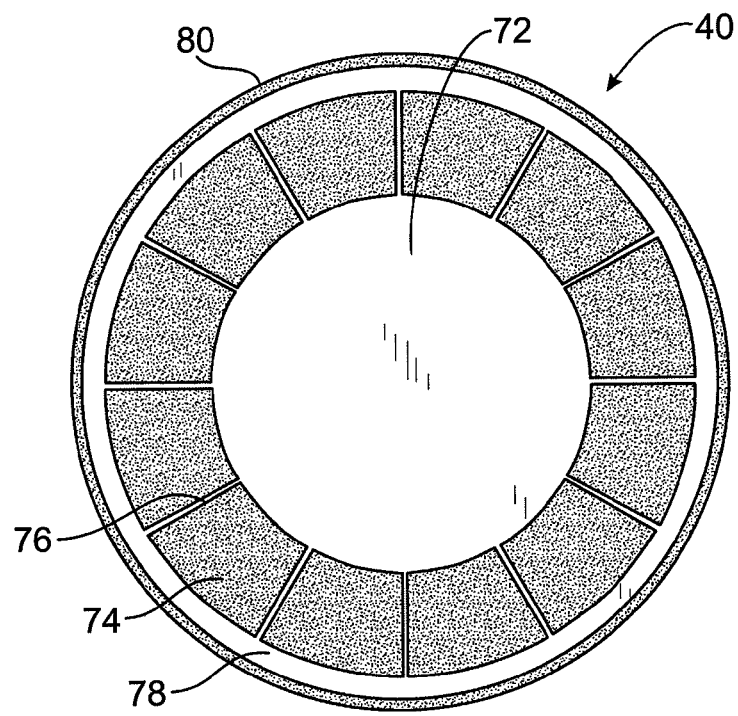
FIG. 13 is a top plan view of one embodiment of a piezoelectric element in accordance with the present invention.

As shown in FIG. 13, a thin ring 78 of ceramic material can be provided at the edge. The ring 78 is connected to the central region of ceramic coating 72 by the segments 76. A ring 80 of the metal plate extends radially outward from the ring of ceramic material 78. The O-ring 42 is sized to abut the ring of ceramic material 78 without contacting the metal plate.

Figure 14:
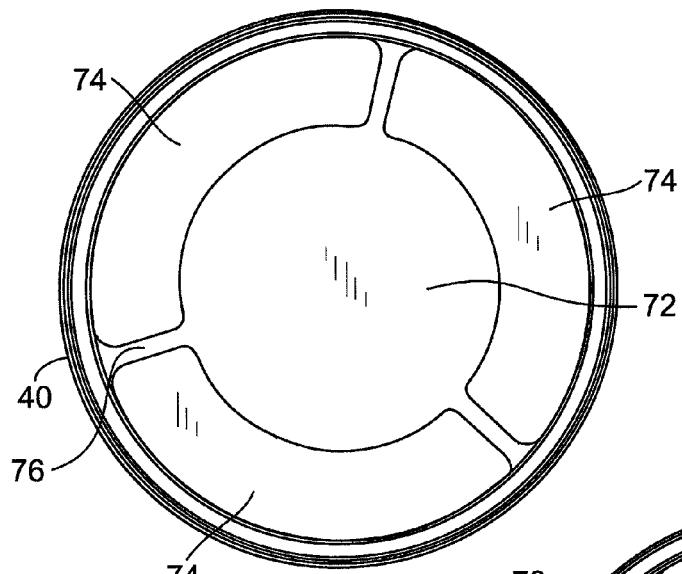
FIG. 14 is a top plan view of another embodiment of a piezoelectric element in accordance with the present invention.

FIG. 13 shows twelve sections 74 devoid of ceramic material. FIG. 14 shows a pattern with three sections 74 devoid of ceramic material. In the embodiment of FIG. 14, the radially extending segments 76 are thicker than the segments used in the embodiment of FIG. 13.

Figure 15:
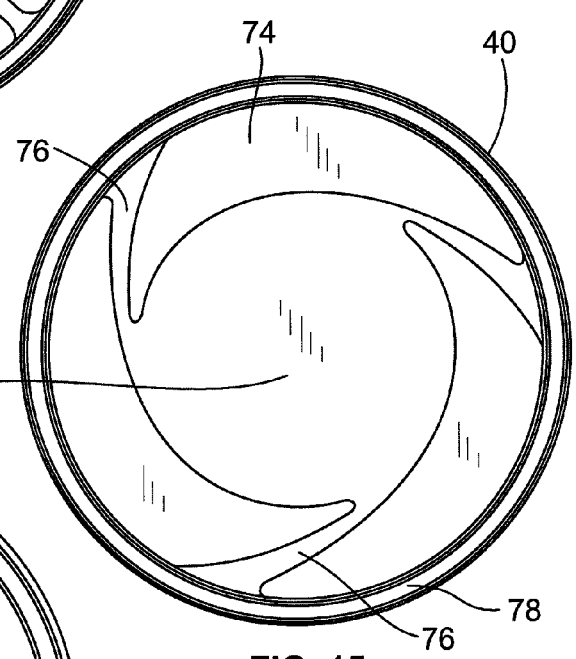
FIG. 15 is a top plan view of another embodiment of a piezoelectric element in accordance with the present invention.

FIG. 15 shows an alternative pattern having three sections 74 devoid of material. In this pattern, the radially extending segments 76 have a curved and flared appearance.

Figure 16:
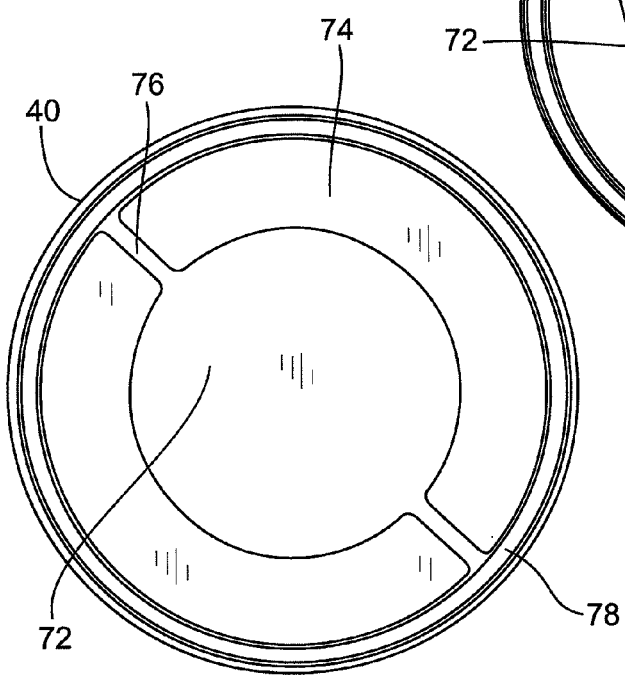
FIG. 16 is a top plan view of another embodiment of a piezoelectric element in accordance with the present invention.
Figure 17:
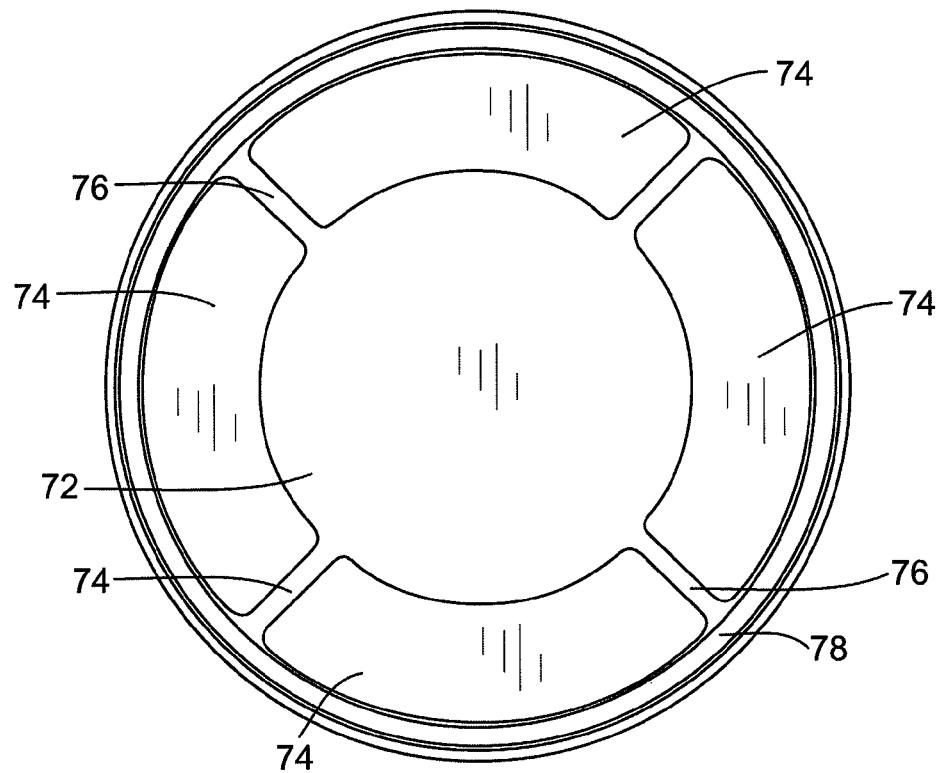
FIG. 17 is a top plan view of another embodiment of a piezoelectric element in accordance with the present invention.

FIGS. 16 and 17 show a piezoelectric element having a ceramic pattern with two sections and four sections 74 devoid of material, respectively. While certain patterns are shown in FIGS. 13-17, other potential patterns could be used.

The sensors or sensor pods 32, along with the sensor pads 10, are preferably used with an array that holds one or more sensor pods 32 in a structure designed to allow for fast and easy placement of the sensor pods 32 at the proper locations of the body. The array structure is designed based on the type of analysis being performed, the number of sensors needed and the approximate location of sensed signals on the body.

Figure 18:
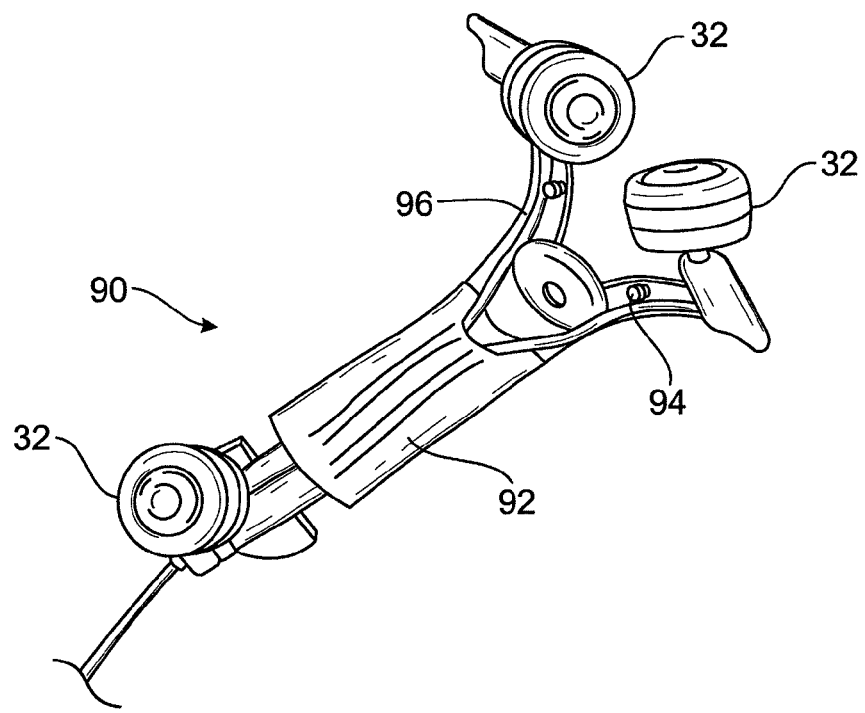
FIG. 18 is a perspective view of a sensor array having three sensors in accordance with apparatuses of the present invention.
Figure 19:
FIG. 19 is a perspective view of the sensor array of FIG. 18 in use.

FIGS. 18 and 19 disclose a sensor array 90 for holding three sensor pods 32. The array 90 includes a generally cylindrical base portion 92 connected to a first sensor pod 32. A first arm 94 connected to a second sensor pod 32 and a second arm 96 connected to a third sensor pod 32 extend upward from an end of the base portion 92.

As shown in FIG. 19, the sensor array is designed to position the first sensor pod 32 over a patient's heart, and to locate the second and third sensor pods 32 proximate the carotid arteries in the patient's neck. Sensed infrasonic signals from these locations can be analyzed to detect potential occlusions. An example of a process for making such an analysis is disclosed in U.S. Pat. No. 7,621,875.

To facilitate proper placement, the first and second arms 94, 96 are designed to be able to twist and flex outward or inward relative to each other and the base portion 92. Additionally, the sensor pods 32 are preferably connected to the array 90 via the swivel ball connector 38 discussed herein. This allows the pods 32 to rotate about the connector and be moved and positioned in the proper sensing locations.

The base portion 92 of the array 90 can be sized or otherwise configured to function as a handle for the array 90. Alternatively, a separate handle structure can be connected to the array 90. The handle allows one (either the patient or someone else, such as a medical technician) to easily grasp the array and hold all three sensors in the proper positions with one hand. Straps are not needed to attach the sensor pods to the body.

The base portion 92 and/or the first arm 94 and/or the second arm 96, can be configured to be extendable (e.g., such as by having telescoping components) to enable one to adjust the size of the array 90. With the extension features and/or the other adjustable features described, the array 90 can be used for a large variation in body sizes and shapes.

The array 90 can be made of plastic or other similar materials. The components (i.e., base portion 92, first arm 94 and second arm 96) of the array 90 are hollow to allow a path for one or more wires or shielded cables to connect to the sensor pods 32 to transmit sensed signals from the pods 32 to a computer or other device for analysis and/or display.

As shown in FIG. 19, the array 90 disclosed is specifically sized and configured to position three sensors on a body for proper sensing of the carotid arteries. However, the structure of the array can be modified for sensing other arteries or veins, or other physiological aspects of a living organism. More or fewer sensors can be used as needed for such structures.

Figure 20:
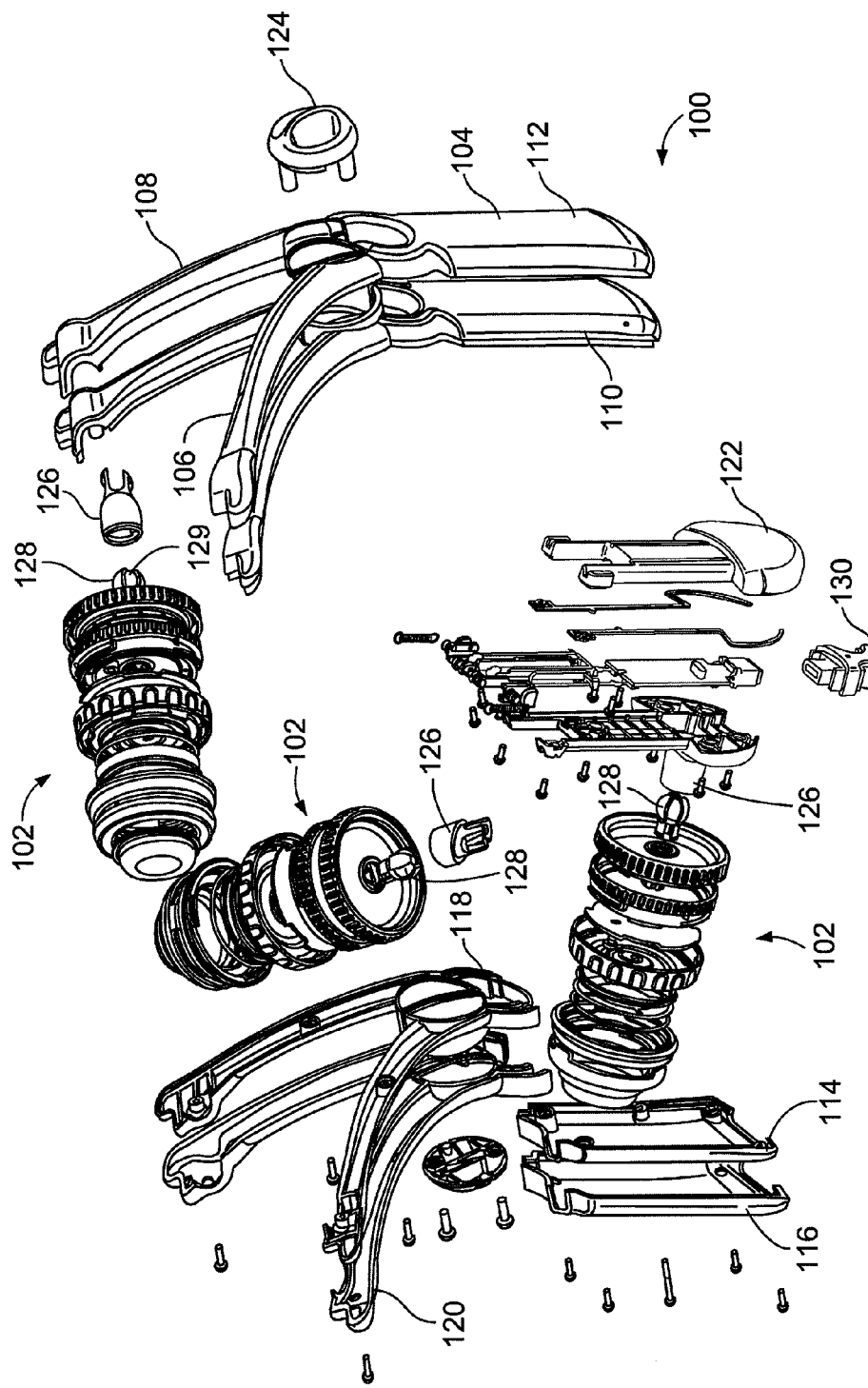
FIG. 20 is an exploded view of a sensor array and three sensors in accordance with one embodiment of the present invention.

FIG. 20 provides an exploded view of a three sensor array 100 with an embodiment of a sensor pod 102 that can be easily replaceable. The array 100 includes a base portion 104 having a first arm 106 and a second arm 108 extending from the top of the base portion 104. As shown, the features of the array 100 include a first side frame structure 110 and an overmold 112. A second side frame structure is broken into two pieces, a second side base portion 114 and an overmold base portion 116, and a second side arm portion 118 and second side overmold portion 120. En extendable tongue 122 is maintained in the base portion 104 between the first side frame structure and second side frame structure. A circular knob 124 is positioned at the juncture of the first and second arms 106, 108 with the base portion 104. Twisting of the knob 124 causes the arms 106, 108 to flex outward or inward, and holds the arms in the flexed position.

A connector element 126 is positioned at the distal ends of the first and second arms 106, 108, and in the base portion 104. The connector is configured to receive a swivel ball connector 128 on the sensor pod 102. Other connection elements can be used. Also, it is possible for the connection elements to be reversed (place the swivel ball on the array and the receiving structure on the pod).

The swivel ball 128 of the sensor pod 102 is formed in a plurality of segments 129 that can flex relative to each other. This allows the swivel ball 128 to snap-fit into the connector element 126 at the base of the pod 102. This enables one to easily remove and replace a new sensor pod when necessary. It is anticipated that a new sensor pod will be needed after every 50-100 uses. New pads are used after each use.

As is evident in FIG. 20, the array 100 has an essentially hollow construction. This enables shielded cables to connect to the sensor pods and travel to central cable 130 plugged into the bottom of the base portion 104.

Figure 22:
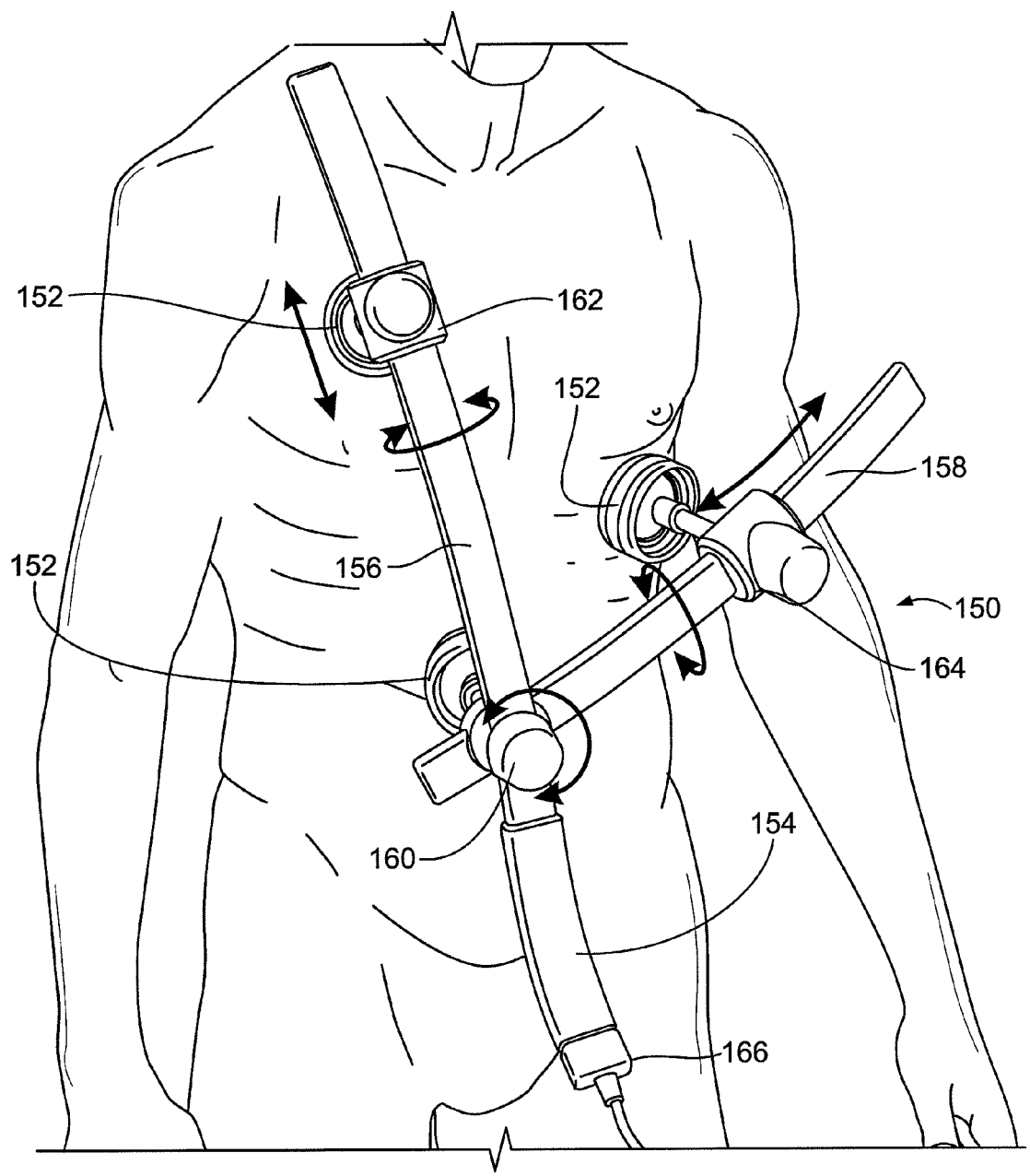
FIG. 22 is a perspective view of an alternative sensor array positioned for use on a patient.

FIG. 22 illustrates another embodiment of an array structure 150 for positioning three sensor pods 152. The array 150 includes a handle or base portion 154 having a first arm 156 extending from the handle 154. A second arm 158 is connected to the first arm 156 proximate the handle 154 by a rotatable connector 160.

A first sensor pod 152 is connected to the first arm 156 by a connector 162. Similarly, a second sensor pod 152 is connected to the second arm by a connector 164. The connectors 162, 164 are mounted to the respective arms 156, 158 and (as indicated by the arrows) are configured to be slideable up and down the arms and to be able to rotate about the arms in order to position the pods 152 in the appropriate positions.

A third sensor pod 152 is connected to the second arm 158 at the juncture where the second arm is connected to the first arm 156. A cable 166 is plugged into an end of the handle 154 for transmitting sensed signals to a computing and/or display device.

Figure 23:
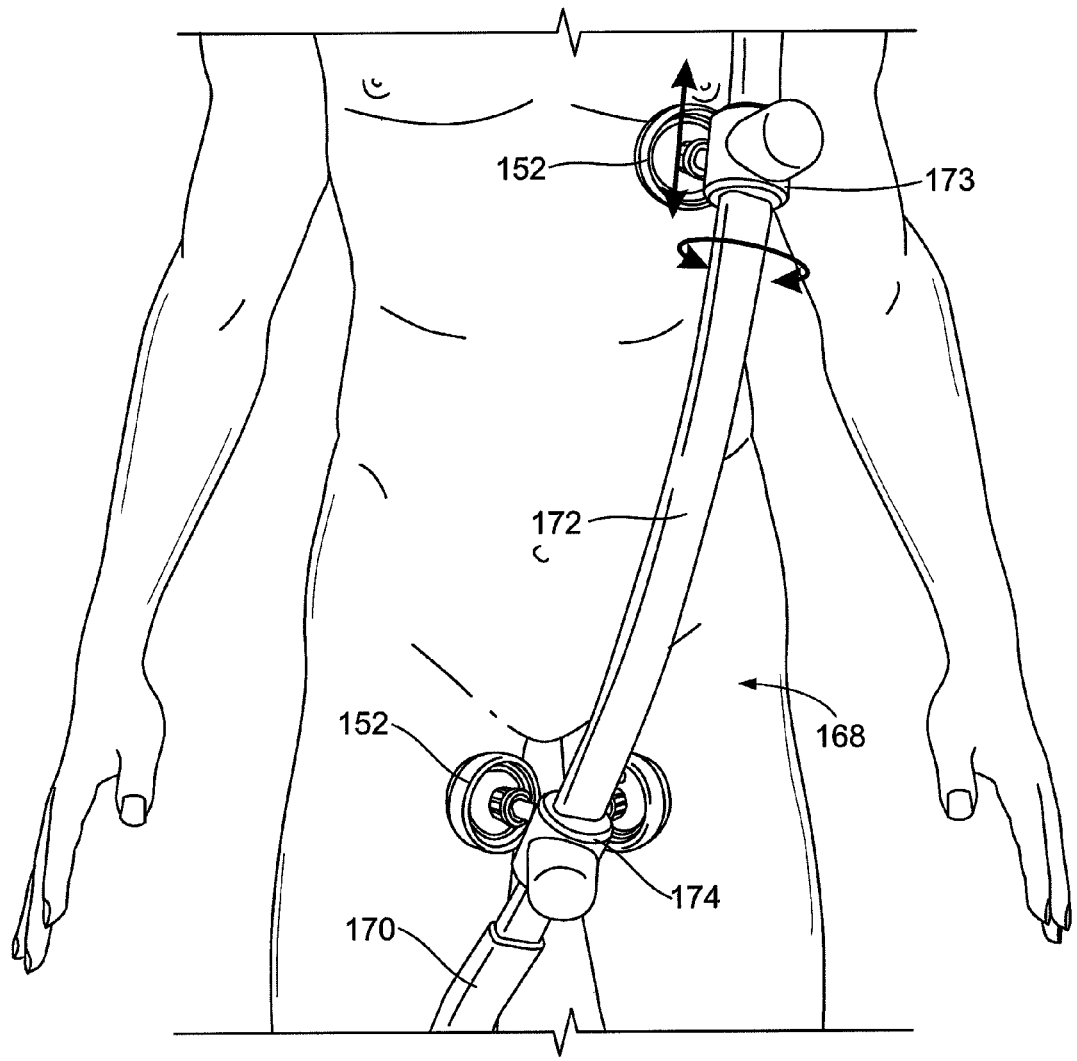
FIG. 23 is a perspective view of another alternative sensor array positioned for use on a patient.

FIG. 23 illustrates yet another array structure 168 for holding three sensor pods 152 (to sense signals from the femoral arteries). The array 168 includes a handle 170 and a single arm 172 extending upward from the handle 170. A first sensor pod 152 is connected at a distal end of the arm 172 (from the handle 170) by a connector 173 similar to the connectors of FIG. 22. A double connector 174 is used to connect two sensor pods 152 proximate the handle 170. While the handle is shown below the double sensor connector 174, a patient or medical technician can grasp a mid-section of the arm 172 to keep the sensors in place during testing.

Figure 24:
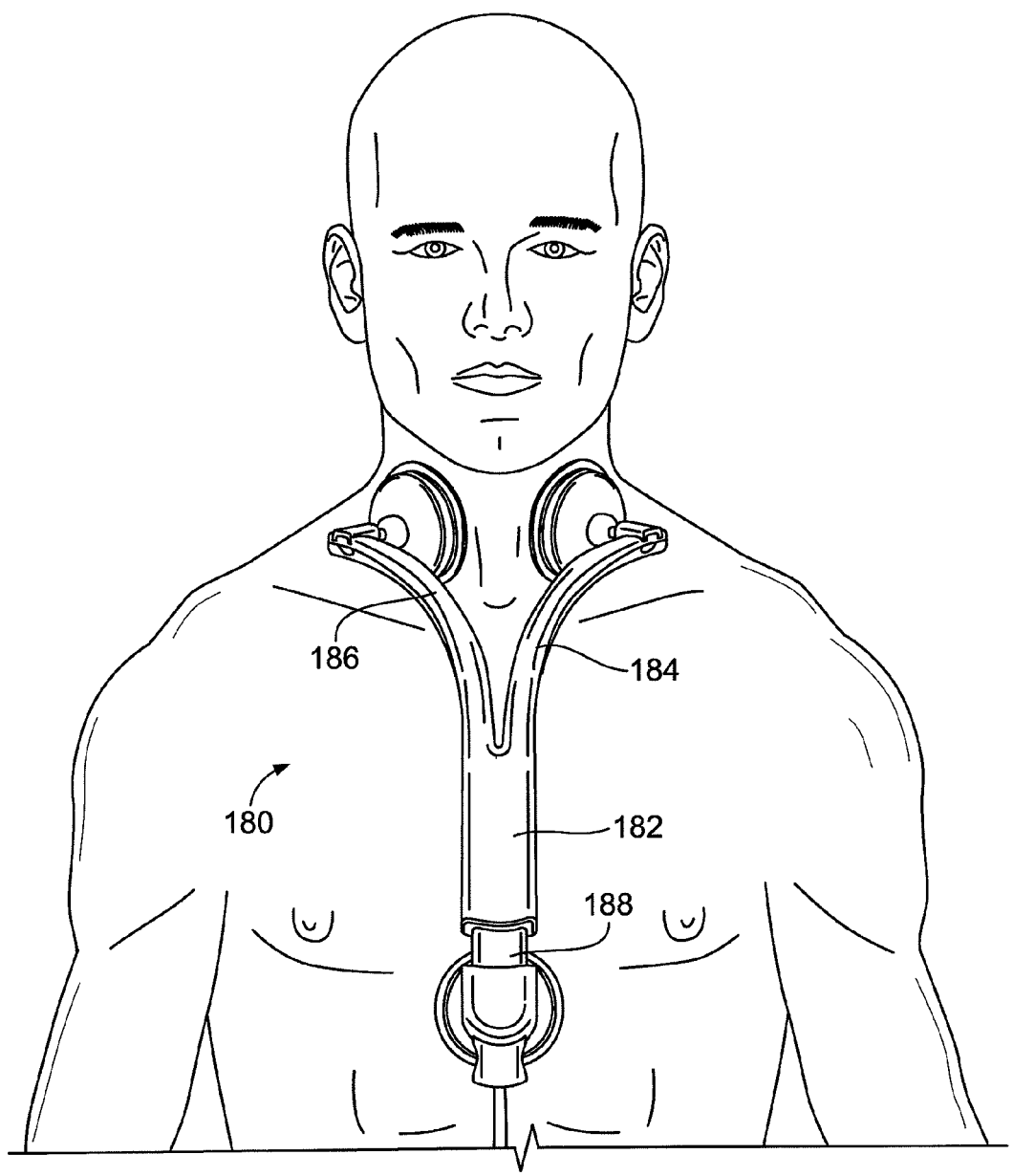
FIG. 24 is a front perspective view of another alternative sensor array positioned for use on a patient.
Figure 25:
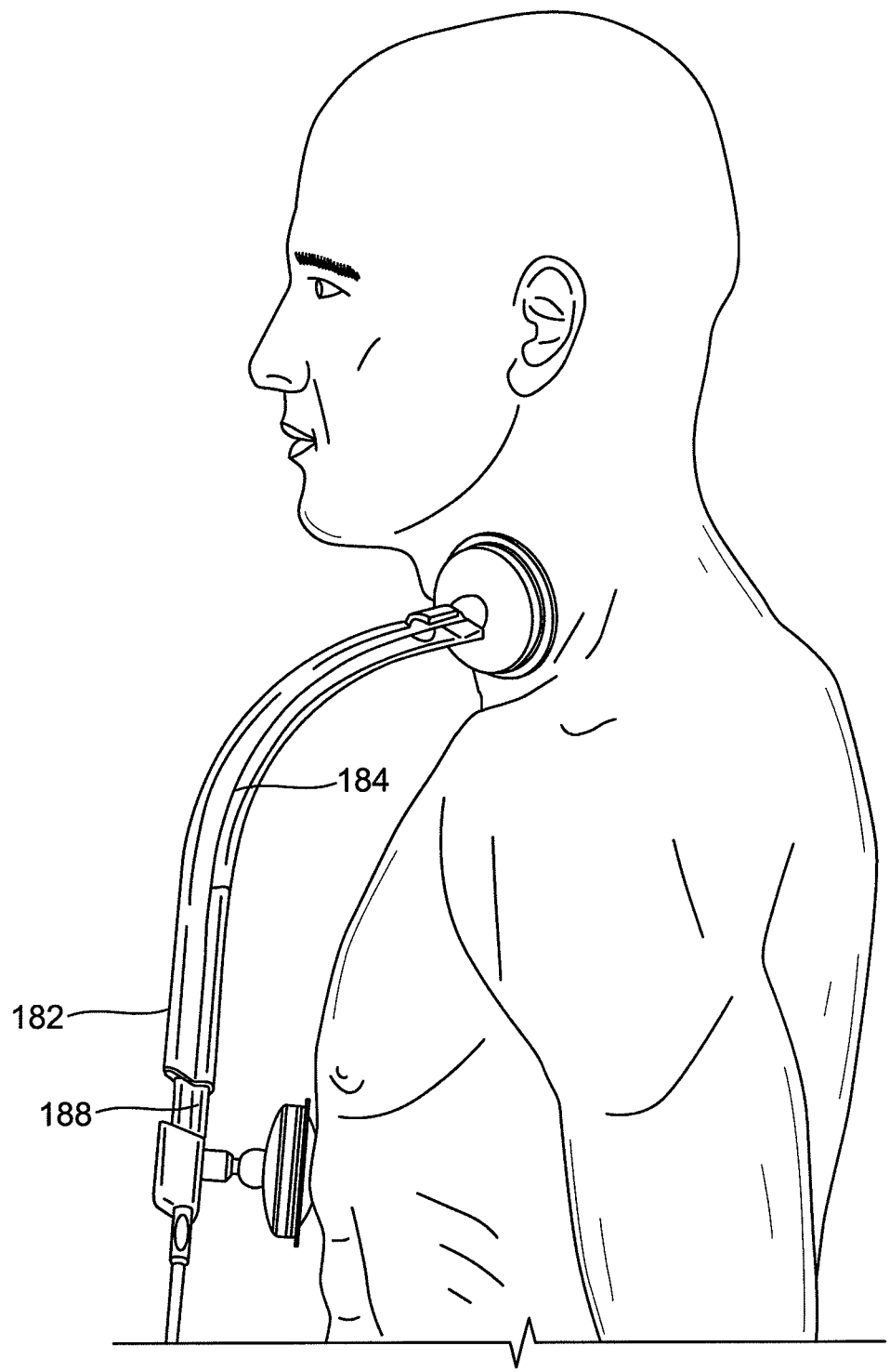
FIG. 25 is a side perspective view of the array of FIG. 24.

FIGS. 24 and 25 disclose another embodiment of an array structure 180 having a base portion 182 and a first arm 184 and a second arm 186 extending outward from an end of the base portion 182. The base portion 182 includes a tongue 188 that is slideable within an upper portion of the base portion 182. The tongue 188 allows for extension of the base portion 182 to accommodate patients of varying sizes.

Figure 26:
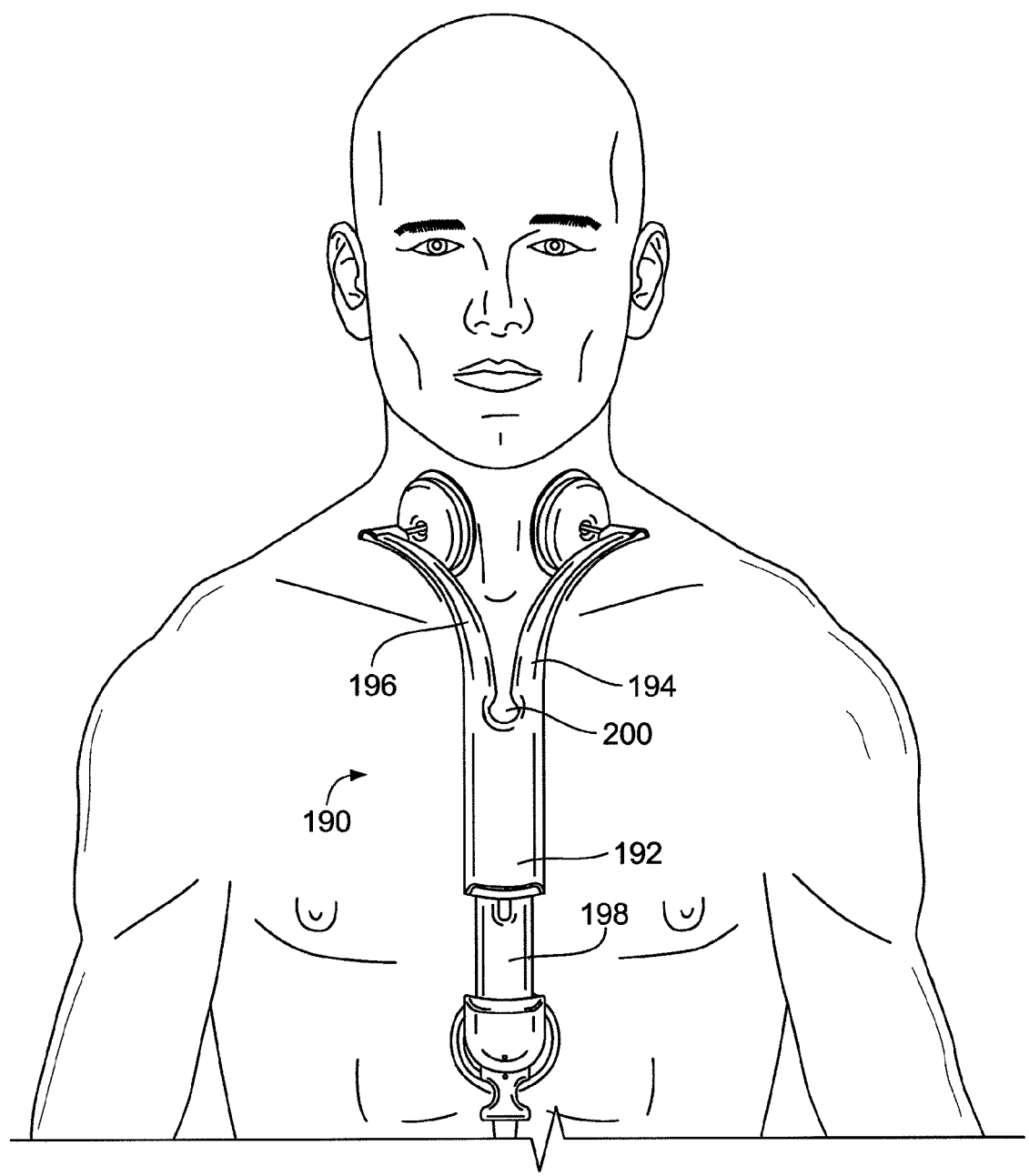
FIG. 26 is a front perspective view of another alternative sensor array positioned for use on a patient.
Figure 27:
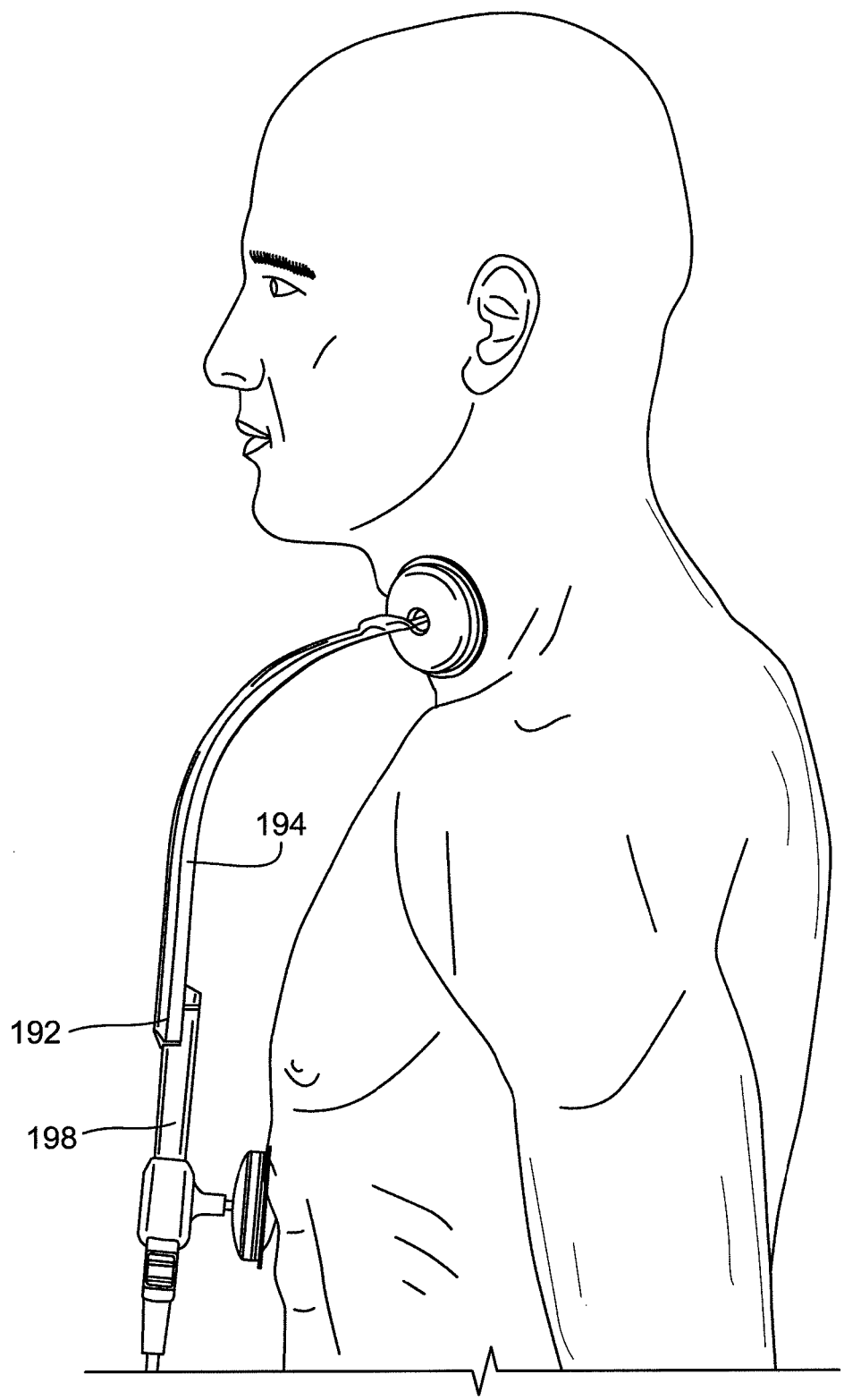
FIG. 27 is a side perspective view of the array of FIG. 26.

FIGS. 26 and 27 disclose yet another array structure 190 having a base portion 192 and a first arm 194 and a second arm 196 extending outward from an end of the base portion 192. The base portion 192 also includes a tongue 198 slidably engaging the base portion 192. However, unlike the embodiment of FIGS. 24 and 25, the tongue 198 utilizes a sliding mechanism wherein the tongue 198 is not contained completely within the base portion 192.

As shown in FIG. 26, a generally curvilinear cut-out portion 200 is provided at the juncture where the arms 194, 196 connect to the base portion 192. This may provide additional flexibility allowing for easier adjustment of the arms.

Figure 28:
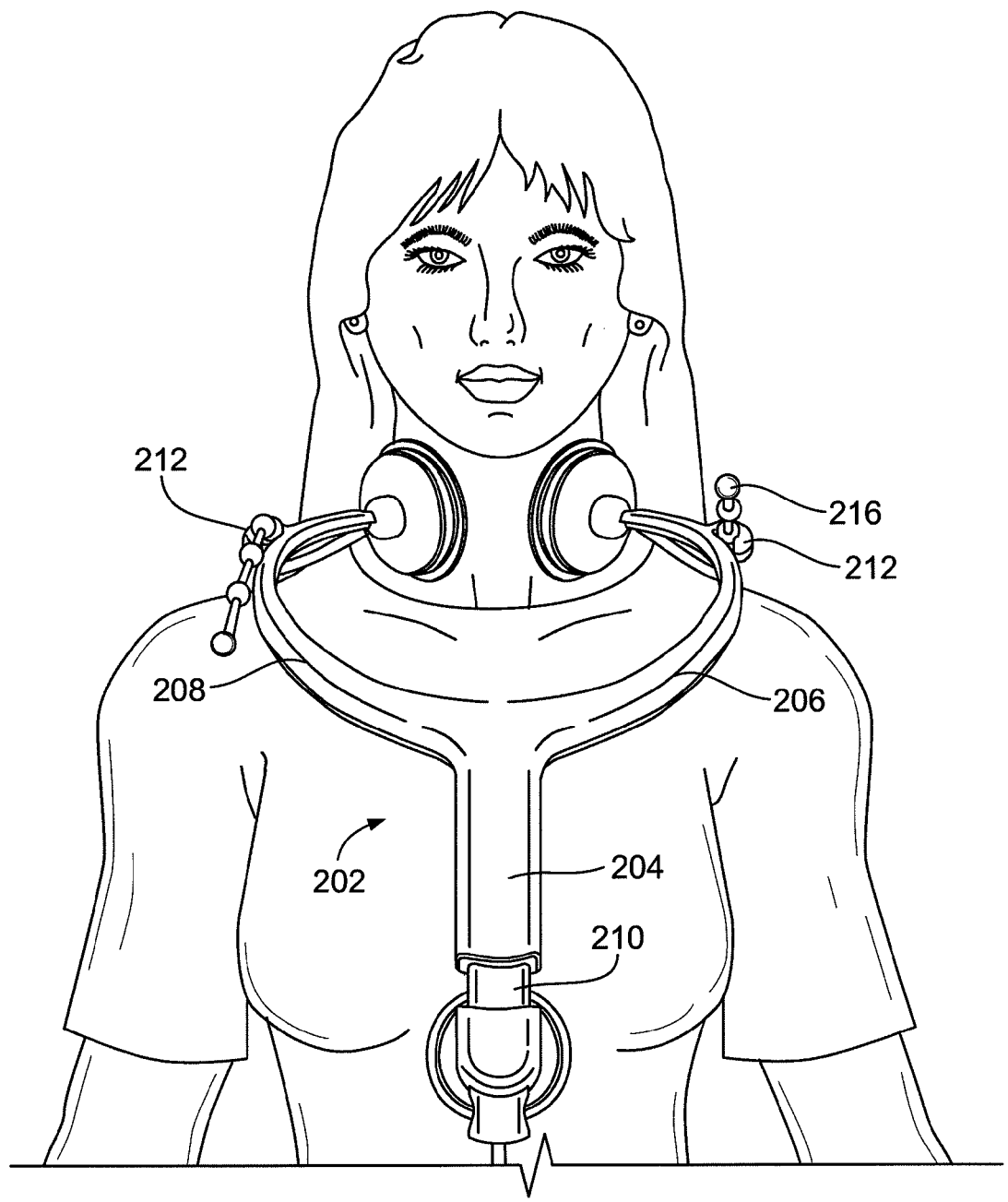
FIG. 28 is a front perspective view of another alternative sensor array positioned for use on a patient; and, FIG. 29 is a side perspective view of the array of FIG. 28.
Figure 29:
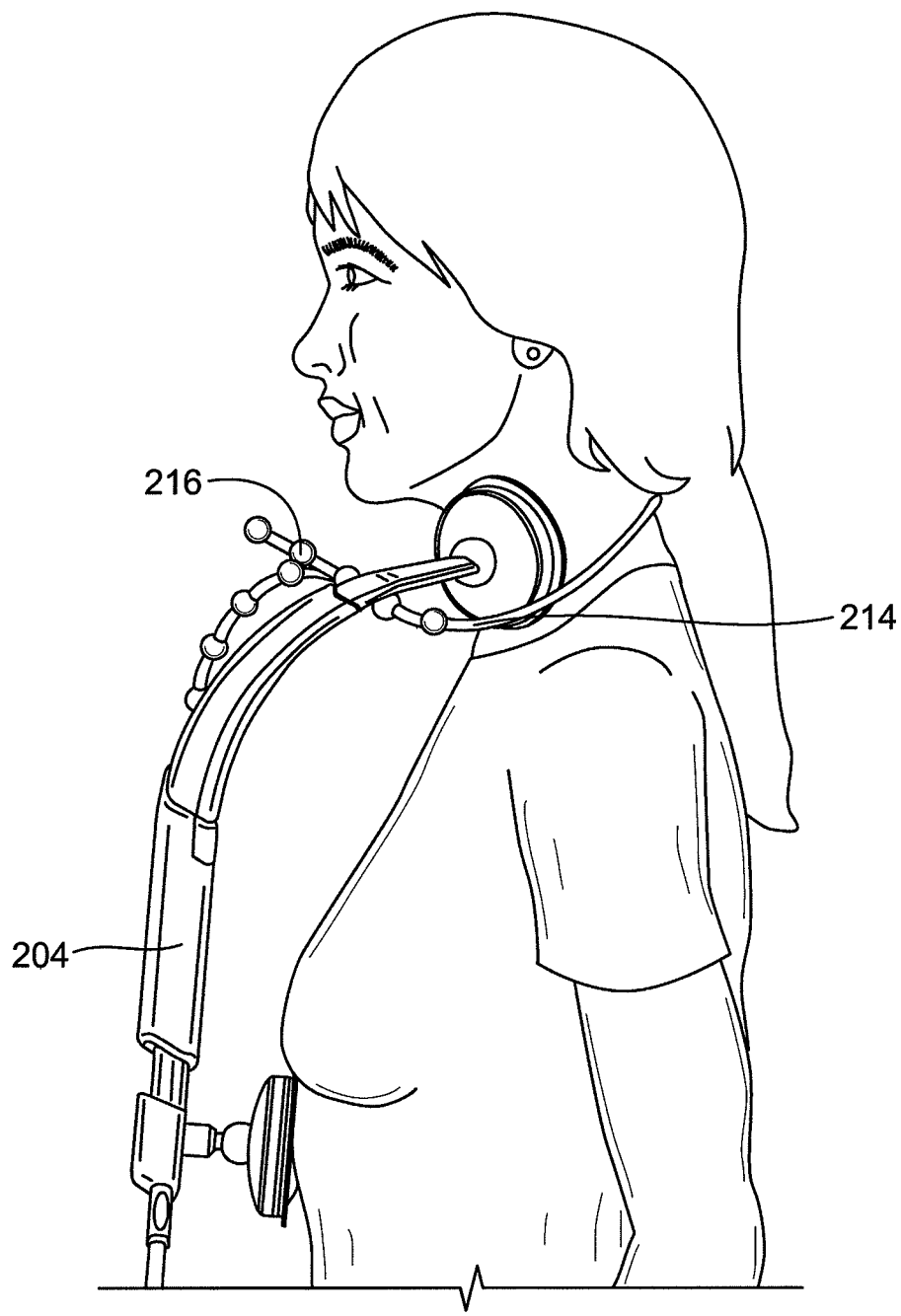

FIGS. 28 and 29 disclose a further embodiment of an array structure 202 having a base portion 204 and a first arm 206 and a second arm 208 extending outward from an end of the base portion 204. The base portion 204 includes a tongue 210 that is slideable within an upper portion of the base portion 204. Notably, the arms 206, 208 have a greater degree of curvature than other embodiments shown in the Figures.

Each arm 206, 208 includes a hook segment 212 or other similar connector extending outward from the arm. The hook segment 212 is provided for connection to a necklace attachment 214 made from a soft thermoplastic rubber or other similar or suitable material. The necklace attachment includes a plurality of spaced apart beads 216 (e.g., approximately 0.8 inches apart) that can be used to adjustably hold the array in place as shown. In place of the beads 216, other configurations (e.g., loops) can be used to adjust the necklace.

While a touch panel PC is a preferred computing unit, any computer or computing system capable of running and displaying the processes described herein can be utilized with the components discussed. Additionally, both wired and/or wireless technology may be utilized with certain of the components of the system. Other components may require a shielded cable to avoid interference in the signal being transmitted.

Many modifications and variations of the present invention are possible in light of the above teachings.

We claim:

1. A second pod for sensing acoustic signal comprising:
   a housing having an interior chamber and a circular opening at one end, and a swivel connector at an opposing end of the housing configured for attachment to a support structure for adjustably moving the sensor pod in multiple directions;
   a piezoelectric element in the form of a circular disk having a first side and an opposing second side contained in the interior chamber of the housing and aligned with the circular opening;
   an acoustic coupling pad having a flat surface portion on a first side contacting the first side of the piezoelectric element and a body contacting portion on a second side extending through the circular opening in the housing, and portion of the body contacting portion extending outward from the opening in the housing;
   a first O-ring positioned on and in contact with the first side of the piezoelectric element; and,
   a second O-ring positioned on and in contact with the second side of the piezoelectric element and wherein the second O-ring includes a circumferential groove positioned so that an edge of the piezoelectric elements sits in the groove.

2. The sensor pod of claim 1 wherein the housing comprises a first upper housing portion connected to a second lower housing portion.

3. The sensor pod of claim 1 wherein the acoustic coupling pad comprises a gel material and includes an outwardly concave portion in a centrally located portion of the body contacting portion.

4. The sensor pod of claim 3 further comprising an amplifier circuit electrically coupled to the piezoelectric element contained in the interior chamber of the housing.

5. The sensor pod of claim 1 wherein the first O-ring comprises an electrically conductive material electrically connecting the piezoelectric element and a computing device.

6. The sensor pod of claim 5 wherein the first O-ring is a metalized rubber.

7. The sensor pod of claim 5 having a first conductive contact element in the housing electronically coupled to the first O-ring for transmitting signals generated by the piezoelectric element.

8. The sensor pod of claim 1 wherein the pod is configured to sense infrasonic acoustic signals.

9. The sensor pod of claim 1 wherein the piezoelectric element comprises a metal plate having a plurality of discrete portions of ceramic material contacting the first side of the plate.

10. The sensor pod of claim 1 wherein the swivel connector extends from a bottom portion of the housing.

11. A sensor pod for sensing infrasonic acoustic signals comprising:
    a sensor housing having an internal chamber and an opening;
    a piezoelectric element mounted in the internal chamber, the piezoelectric element comprising a metal plate having a first side and an opposing second side, the first side having a piezo-type material coating at least a portion of the first side, wherein the piezoelectric element spans across the opening dividing the internal chamber into an outer chamber portion configured to receive an acoustic coupling pad and an inner chamber portion;

an acoustic coupling pad comprising a gel material and having a flat surface portion on a first side contacting the first side of the piezoelectric element and a body contacting portion on a second side extending through the opening in the housing, and a portion of the body contacting portion extending outward from the opening in the housing, the coupling pad including an outwardly concave portion in a centrally located portion of the body contacting portion;

a first O-ring positioned on and in contact with the first side of the piezoelectric element, and a second O-ring positioned on and in contact with the second side of the piezoelectric element, wherein the second O-ring includes a circumferential groove positioned so that an edge of the piezoelectric element sits in the groove; and, an amplifier circuit mounted in the inner chamber portion of the housing and electrically coupled to the piezoelectric element wherein the housing comprises a metal surface around the inner chamber portion such that the metal surface of the housing and the metal plate of the piezoelectric element form a faraday cage around the amplifier circuit.

12. The sensor pod of claim 11 wherein the housing comprises a first housing portion and a second housing portion and wherein the inner chamber is formed in the second housing portion.

13. The sensor pod of claim 12 further comprising a swivel connector extending from a portion of the second housing portion.

14. The sensor pod of claim 11 wherein the piezoelectric element is a circular disk.

15. The sensor pod of claim 11 wherein the first and second O-rings comprise an electrically conductive material.

16. The sensor pod of claim 15 wherein the first and second O-rings are formed from a metalized rubber.

17. The sensor pod of claim 11 wherein the acoustic coupling pad has a low durometer value.

18. A sensor pod for sensing acoustic signals comprising:

a housing having an interior chamber and a circular opening at one end, and a swivel connector at an opposing end for adjustably moving the sensor pod;

a piezoelectric element in the form of a circular disk having a first side and an opposing second side contained in the interior chamber of the housing an aligned with the circular opening;

an acoustic coupling pad having a flat surface portion on a first side contacting the first side of the piezoelectric element and a body contacting portion on a second side extending through the circular opening in the housing;

a first O-ring positioned on and in contact with the first side of the piezoelectric element; and, a second O-ring positioned on and in contact with the second side of the piezoelectric element and wherein the second O-ring includes a circumferential groove positioned so that an edge of the piezoelectric element sits in the groove.

* * * * *

UNITED STATES PATENT AND TRADEMARK OFFICE
CERTIFICATE OF CORRECTION

| | |
|---|---|
| PATENT NO. | : 9,101,274 B2 |
| APPLICATION NO. | : 13/167567 |
| DATED | : August 11, 2015 |
| INVENTOR(S) | : Peter Bakema et al. |

It is certified that error appears in the above-identified patent and that said Letters Patent is hereby corrected as shown below:

Claims

Column 14, line 8, Claim 1, the word "second" should read --sensor--.

Signed and Sealed this
Twelfth Day of January, 2016

Michelle K. Lee
*Director of the United States Patent and Trademark Office*